(12) United States Patent
Lee et al.

(10) Patent No.: US 8,735,110 B2
(45) Date of Patent: May 27, 2014

(54) PSEUDOMONAS AERUGINOSA STRAIN DEVELOPED FOR IMPROVING FATTY ACID CONTENT, AND METHOD OF MANUFACTURING THE SAME

(75) Inventors: Jin-Won Lee, Seoul (KR); Sun-Hee Lee, Seoul (KR); Eun-Young Jeon, Seoul (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 0 days.

(21) Appl. No.: 13/642,127

(22) PCT Filed: Mar. 7, 2011

(86) PCT No.: PCT/KR2011/001554
§ 371 (c)(1),
(2), (4) Date: Oct. 19, 2012

(87) PCT Pub. No.: WO2011/132852
PCT Pub. Date: Oct. 27, 2011

(65) Prior Publication Data
US 2013/0034886 A1    Feb. 7, 2013

(30) Foreign Application Priority Data

Apr. 22, 2010  (KR) .................. 10-2010-0037546
Feb. 17, 2011  (KR) .................. 10-2011-0014270

(51) Int. Cl.
*C12P 7/64*    (2006.01)
*C12N 1/12*    (2006.01)

(52) U.S. Cl.
USPC ....................................... 435/134; 435/257.2

(58) Field of Classification Search
USPC ............................................. 435/134, 257.2
See application file for complete search history.

(56) References Cited

U.S. PATENT DOCUMENTS

2011/0047862 A1    3/2011 Mayeur et al.

OTHER PUBLICATIONS

Ohlrogge, J. et al. 'Alteration of acyl-acyl carrier protein pools and acetyl-CoA carboxylase expression in *Escherichia coli* by a plant medium chain acyl-acyl carrier protein thioesterase' Archives of Biochemistry and Biophysics. vol. 317(1), pp. 185-190 (Feb. 20, 1995).
Davis, M. S. et al. 'Overproduction of acetyl-CoA carboxylase activity increases the rate of fatty acid biosynthesis is *Escherichia coli*' Journal of Biological Chemistry. vol. 275(37), pp. 28593-28598 (Sep. 15, 2000).
Fujita, Y. et al. 'Regulation of fatty acid metabolism in bacteria' Molecular Microbiology. vol. 66(4), pp. 829-839 (Oct. 2, 2007).
NCBI GenBank No. NP_251658 'malonyl-CoA-[acyl-carrier-protein] transacylase [*Pseudomonas aeruginosa* PA01]' Mar. 31, 2010.
NCBI GenBank No. YP_598492 'acy-acyl-carrier protein thioesterase [*Streptococcus pyogenes* MGAS10270]' May 9, 2006.
NCBI GenBank No. NP_252329 'acetyl-CoA carboxylase carboxyltransferase subunit alpha[*Pseudomonas aeruginosa* PA01]' Mar. 31, 2010.

*Primary Examiner* — Maryam Monshipouri
(74) *Attorney, Agent, or Firm* — Lexyoume IP Meister, PLLC

(57) ABSTRACT

Disclosed are novel *Pseudomonas aeruginosa* strains capable of producing in high yield and preparation methods thereof. The strains anchor an expression vector carrying either or both of a nucleotide sequence coding for acetyl-CoA carboxylase carboxytransferase subunit alpha of *Pseudomonas aeruginosa* and a nucleotide sequence coding for malonyl-CoA-[acyl-carrier-protein] transacylase of *Pseudomonas aeruginosa*, and/or a nucleotide sequence coding for acyl-acyl carrier protein thioesterase of *Streptococcus pyogenes*. The recombinant *Pseudomonas aeruginosa* strains are genetically stable and have high lipid or fatty acid contents, thus being applicable to the mass production of fatty acids.

26 Claims, 10 Drawing Sheets

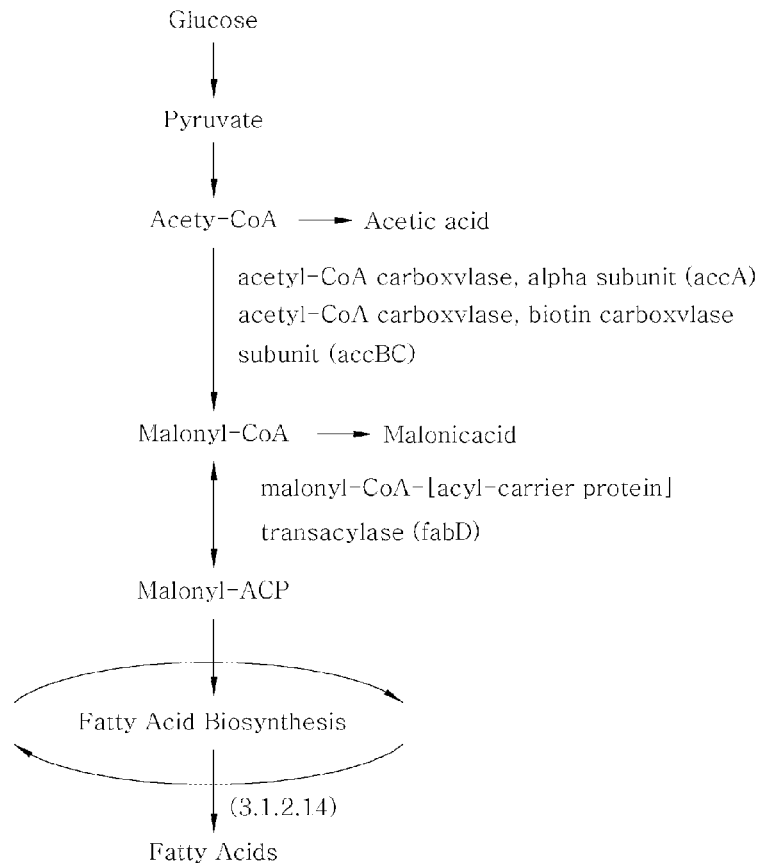
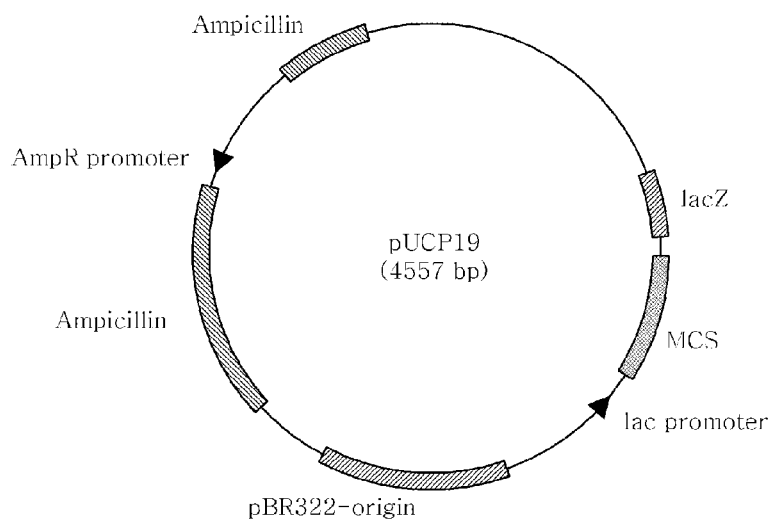

SEQUENCE LISTING

```
<160> NUMBER OF SEQ ID NOS: 13

<210> SEQ ID NO 1
<211> LENGTH: 316
<212> TYPE: PRT
<213> ORGANISM: Pseudomonas aeruginosa

<400> SEQUENCE: 1

Met Asn Pro Asn Phe Leu Asp Phe Glu Gln Pro Ile Ala Asp Leu Gln
 1               5                  10                  15

Ala Lys Ile Glu Glu Leu Arg Leu Val Gly Asn Asp Asn Ala Leu Asn
            20                  25                  30

Ile Ser Asp Glu Ile Ser Arg Leu Gln Asp Lys Ser Lys Ala Leu Thr
        35                  40                  45

Glu Asn Ile Phe Gly Asn Leu Ser Ser Trp Gln Ile Ala Gln Leu Ala
    50                  55                  60

Arg His Pro Lys Arg Pro Tyr Thr Leu Asp Tyr Ile Gly Tyr Leu Phe
65                  70                  75                  80

Ser Asp Phe Glu Glu Leu His Gly Asp Arg His Phe Ala Asp Asp Pro
                85                  90                  95

Ala Ile Val Gly Gly Val Ala Arg Leu Asp Gly Ser Pro Val Met Val
            100                 105                 110

Ile Gly His Gln Lys Gly Arg Glu Val Arg Glu Lys Val Arg Arg Asn
        115                 120                 125

Phe Gly Met Pro Arg Pro Glu Gly Tyr Arg Lys Ala Cys Arg Leu Met
    130                 135                 140
```

| | | | | | | | | | | | | | | | |
|---|---|---|---|---|---|---|---|---|---|---|---|---|---|---|---|
|Glu|Met|Ala|Glu|Arg|Phe|Lys|Met|Pro|Ile|Leu|Thr|Phe|Ile|Asp|Thr|
|145| | | | |150| | | | |155| | | | |160|

Pro Gly Ala Tyr Pro Gly Ile Asp Ala Glu Glu Arg Gly Gln Ser Glu
               165                  170                175

Ala Ile Ala Trp Asn Leu Arg Val Met Ala Arg Leu Lys Thr Pro Ile
           180                  185                  190

Ile Ala Thr Val Ile Gly Glu Gly Gly Ser Gly Gly Ala Leu Ala Ile
        195                  200                205

Gly Val Cys Asp Gln Leu Asn Met Leu Gln Tyr Ser Thr Tyr Ser Val
        210                  215              220

Ile Ser Pro Glu Gly Cys Ala Ser Ile Leu Trp Lys Thr Ala Glu Lys
225              230                235           240

Ala Pro Glu Ala Ala Glu Ala Met Gly Ile Thr Ala Glu Arg Leu Lys
           245                  250              255

Gly Leu Gly Ile Val Asp Lys Val Ile Asp Glu Pro Leu Gly Gly Ala
        260                  265              270

His Arg Asp Pro Ala Ser Met Ala Glu Ser Ile Arg Gly Glu Leu Leu
       275                  280              285

Ala Gln Leu Lys Met Leu Gln Gly Leu Glu Met Gly Glu Leu Leu Glu
       290                  295              300

Arg Arg Tyr Asp Arg Leu Met Ser Tyr Gly Ala Pro
305              310                315

<210> SEQ ID NO 2
<211> LENGTH: 951
<212> TYPE: DNA
<213> ORGANISM: Pseudomonas aeruginosa

<400> SEQUENCE: 2

```
atgaacccga actttcttga tttcgaacag ccgatcgccg acctgcaagc caagatcgaa      60
gagctgcgcc tggtgggcaa cgacaatgcg ctgaacatca gcgacgaaat ctcgcgtctg     120
caggacaaga gcaaggcgct caccgaaaac atcttcggca atctgtccag ttggcagatc     180
gcccagctcg cgcgccatcc caagcgtccc tataccctcg actacatcgg ctacctgttc     240
agcgatttcg aggaactgca cggcgaccgg catttcgccg acgacccggc gatcgtcggc     300
ggcgttgccc gcctcgacgg ttccccggtg atggtcatcg ccaccagaa gggccgcgaa      360 gtccgtgaga aggtccggcg caacttcggc atgccgcgtc cggaaggcta tcgcaaggcc     420
tgccgcctga tggaaatggc cgaacgcttc aagatgccga tcctcacctt catcgacacg     480
cccggcgcct acccggggat cgatgccgag aacgcggcc agagcgaggc gatcgcctgg      540
aacctgcggg tgatggcgcg actgaagacg ccgatcatcg ccaccgtgat cggcgagggc     600
ggttccggcg gcgcgctggc catcggtgtc tgcgaccagt tgaacatgct gcaatactcc     660
acctattcgg tgatctcgcc ggaaggctgc gcctccatcc tctggaagac cgccgagaag     720
gcgccggaag ccgccgaggc catgggcatc accgccgagc gcctgaaagg cctgggcatc     780
gtcgacaagg tcatcgacga accgctgggc ggcgcccatc gcgatccggc gagcatggcc     840
gaatcgatcc gtggcgaact gctggcgcaa ctgaagatgc tccagggcct ggaaatgggt     900
gagttgctgg agcgtcgtta cgaccgcctg atgagctacg gcgcgccgta a             951
```

<210> SEQ ID NO 3
<211> LENGTH: 312
<212> TYPE: PRT
<213> ORGANISM: Pseudomonas aeruginosa

```
<400> SEQUENCE: 3

Met Ser Ala Ser Leu Ala Phe Val Phe Pro Gly Gln Gly Ser Gln Ser
 1               5                  10                  15

Leu Gly Met Leu Ala Glu Leu Gly Ala Gln Gln Ala Leu Val Arg Asp
             20                  25                  30

Thr Phe Ala Glu Ala Ser Glu Ala Leu Gly Tyr Asp Leu Trp Ala Leu
         35                  40                  45

Val Gln Asn Gly Pro Glu Glu Arg Leu Asn Gln Thr Asp Lys Thr Gln
     50                  55                  60

Pro Ala Ile Leu Thr Val Ser Ile Ala Leu Trp Arg Leu Trp Leu Ala
 65                  70                  75                  80

Glu Gly Gly Ala Arg Pro Ala Phe Val Ala Gly His Ser Leu Gly Glu
                 85                  90                  95

Tyr Ser Ala Leu Val Ala Ala Glu Ser Leu Ala Phe Ala Asp Ala Val
            100                 105                 110

Lys Leu Val Glu Arg Arg Gly Gln Leu Met Gln Gln Ala Val Pro Ala
        115                 120                 125

Gly Gln Gly Gly Met Ala Ala Ile Leu Gly Leu Glu Asp Ala Asp Val
    130                 135                 140

Leu Ala Ala Cys Ala Glu Ala Ala Gln Gly Glu Val Val Ser Ala Val
145                 150                 155                 160

Asn Phe Asn Ala Pro Gly Gln Val Val Ile Ala Gly Ala Ala Ala Ala
                165                 170                 175

Val Glu Arg Ala Ile Glu Ala Cys Lys Ala Arg Gly Ala Lys Arg Ala
            180                 185                 190

Val Ala Leu Pro Val Ser Val Pro Ser His Cys Glu Leu Met Arg Pro
        195                 200                 205

Ala Ala Glu Gln Phe Ala Ala Ser Val Glu Ser Leu Gln Trp Gln Ala
    210                 215                 220

Pro Lys Ile Ser Leu Val Gln Asn Val Ser Ala Ala Val Pro Ala Asp
225                 230                 235                 240

Leu Asp Thr Leu Arg Arg Asp Leu Leu Ala Gln Leu Tyr Ser Pro Val
                245                 250                 255

Arg Trp Val Glu Ser Ile Gln Leu Leu Ala Glu Lys Gly Val Thr Glu
            260                 265                 270

Leu Val Glu Cys Gly Pro Gly Lys Val Leu Ala Gly Leu Asn Arg Arg
        275                 280                 285

Cys Ala Lys Gly Ile Asn Thr His Gly Leu Asp Gly Val Glu Ala Phe
    290                 295                 300

Ala Ala Thr Arg Ala Ala Leu Ala
305                 310

<210> SEQ ID NO 4
<211> LENGTH: 939
<212> TYPE: DNA
<213> ORGANISM: Pseudomonas aeruginosa

<400> SEQUENCE: 4
atgtctgcat ccctcgcatt cgtcttccct ggccagggtt cgcaatccct cggcatgctg      60
gccgagctgg gcgcccagca ggcgctggtg cgcgatacct cgccgaggc ctccgaggcg     120 ctcggttacg acctttgggc gctggtccag aatggtcctg aagagcgcct gaaccagacc     180
gacaagaccc agccggccat ccttacggtt cgatcgcgc tctggcgcct ctggctggcc     240
gagggcggtg cgcgcccggc gttcgtcgcc gggcacagcc tgggcgaata ttccgcgctg     300
```

-continued

```
gtcgcggccg aaagcctggc gttcgccgat gcggtcaagc tggtcgagcg taggggccaa    360
ctgatgcagc aggcggttcc ggcggggcag ggcggcatgg ccgcgatcct tggcctggaa    420
gacgccgatg tattggcggc ctgtgccgag gcggcccagg gcgaggtggt cagcgcggtc    480
aacttcaacg cgccggggca ggtagtgatc gccggtgccg cggctgccgt tgagcgtgcc    540
atcgaggcat gcaaggcacg cggcgccaag cgcgcggtgg cgttgccagt cagcgtgccg    600
tcgcattgcg aactgatgcg tccggccgcc gagcagttcg ccgcctcggt cgaaagcctg    660
cagtggcagg cgccgaagat ttcgctggtg cagaacgtca gcgccgccgt gccggctgat    720
ctcgatacgc tgcgccgcga cctgctggca cagctgtaca gcccggttcg ctgggtggag    780
agcatccagc tgctggcgga aaagggcgtc accgagctgg tcgagtgcgg gccgggcaag    840
gtcctggcag gcctcaacag cgctgcgcg aagggcatca tacccatgg cctggatggc     900 gtcgaggcgt tcgccgccac gcgcgccgcc ctggcctga                           939
```

<210> SEQ ID NO 5
<211> LENGTH: 250
<212> TYPE: PRT
<213> ORGANISM: Streptococcus pyogenes

<400> SEQUENCE: 5

```
Met Gly Leu Ser Tyr Gln Glu Glu Leu Thr Leu Pro Phe Glu Leu Cys
  1               5                  10                  15

Asp Val Lys Ser Asp Ile Lys Leu Pro Leu Leu Leu Asp Tyr Cys Leu
             20                  25                  30

Met Val Ser Gly Arg Gln Ser Ala Gln Leu Gly Arg Ser Asn Asn Asn
         35                  40                  45

Leu Leu Val Asp Tyr Lys Leu Val Trp Ile Val Thr Asp Tyr Glu Ile
     50                  55                  60

Thr Ile His Arg Leu Pro His Phe Gln Glu Thr Ile Thr Ile Glu Thr
 65                  70                  75                  80

Lys Ala Leu Ser Tyr Asn Lys Phe Phe Cys Tyr Arg Gln Phe Tyr Ile
                 85                  90                  95

Tyr Asp Gln Glu Gly Gly Leu Leu Val Asp Ile Leu Ala Tyr Phe Ala
            100                 105                 110

Leu Leu Asn Pro Asp Thr Arg Lys Val Ala Thr Ile Pro Glu Asp Leu
        115                 120                 125

Val Ala Pro Phe Lys Thr Asp Phe Val Lys Lys Leu Tyr Arg Val Pro
    130                 135                 140

Lys Met Pro Leu Leu Glu Gln Ser Ile Asp Arg Asp Tyr Tyr Val Arg
145                 150                 155                 160

Tyr Phe Asp Ile Asp Met Asn Gly His Val Asn Asn Ser Lys Tyr Leu
                165                 170                 175

Asp Trp Met Tyr Asp Val Leu Gly Cys Ala Phe Leu Lys Thr His Gln
            180                 185                 190

Pro Leu Lys Met Thr Leu Lys Tyr Val Lys Glu Val Ser Pro Gly Gly
        195                 200                 205

Gln Ile Thr Ser Ser Tyr His Leu Asp Gln Leu Asn Ser Tyr His Gln
    210                 215                 220

Ile Thr Ser Asp Gly Gln Leu Asn Ala Gln Ala Met Ile Glu Trp Arg
225                 230                 235                 240

Ala Ile Lys Gln Thr Glu Ser Glu Ile Asp
                245                 250
```

<210> SEQ ID NO 6

```
<211> LENGTH: 753
<212> TYPE: DNA
<213> ORGANISM: Streptococcus pyogenes

<400> SEQUENCE: 6
atgggattaa gttatcagga ggagttgaca cttcctttg aattatgtga tgtcaaatca      60
gatataaaat tgccccttt attagactat tgtttgatgg tttctggtag acagtctgcg     120
caattaggac gaagtaacaa caaccttta gtcgattaca agcttgtttg gattgtaacg     180
gattatgaga tcactattca tcgcttgcca cattttcaag aaaccatcac cattgaaaca     240
aaagcccttt cctataataa attttttgt tatcgccaat tttatattta tgatcaagag     300 ggggtcttt tagtggatat cttagcctat tttgctttgt taaacccaga tacgcgaaaa     360
gtggcaacta ttccagaaga tttagtagcg ccttttaaga ctgattttgt taaaaagtta     420
taccgtgttc ctaaaatgcc tcttttagaa caatcaattg atcgtgatta ttatgtgcgt     480 tatttttgata ttgatatgaa tggtcatgtc aacaacagta aatatttaga ttggatgtat     540
gatgtgttgg ggtgtgcgtt tttaaaaacg catcagcctc ttaagatgac tttgaaatat     600
gttaaagaag tctcaccagg cggtcaaatt acttccagtt accatttgga ccaattaaat     660
tcttaccatc aaatcacctc agatgggcag ctgaatgccc aagccatgat tgaatggcga     720
gcgattaaac aaacagaaag cgagatagac tag                                  753

<210> SEQ ID NO 7
<211> LENGTH: 4557
<212> TYPE: DNA
<213> ORGANISM: Artificial Sequence
<220> FEATURE:
<223> OTHER INFORMATION: pUCP19 Full Sequence

<400> SEQUENCE: 7
aattacacgc cactggctgt gcttgctggg gtgacggtgg caacggtggc ggccttgctg      60
ggctatcgcg ttggaaagaa acgagggaaa ggggactgat aaaccggtct tagcccctcc     120
ccttggtgtc caaccgctct gtaggcctct caggcgccgc tggtgccgct ggttggacgc     180
caagggtgaa tccgcctcga taccctgatt actcgcttcc tgcgccctct caggcggcga     240
taggggactg gtaaaacggg gattgcccag acgcctcccc cgcccttca ggggcacaaa     300 tgcggcccca cggggccac gtagtggtgc gttttttgcg tttccaccct tttcttcctt     360 ttcccttta aaccttttag gacgtctaca ggccacgtaa tccgtggcct gtagagttta     420
aaaagggacg gatttgttgc cattaaggga cggatttgtt gttaagaagg gacggatttg     480
ttgttgtaaa gggacggatt tgttgtattg tgggacgcag atacagtgtc cccttataca     540
caaggaatgt cgaacgtggc ctcaccccca atggtttaca aaagcaatgc cctggtcgag     600
gccgcgtatc gcctcagtgt tcaggaacag cggatcgttc tggcctgtat agccaggtg     660 aagaggagcg agcctgtcac cgatgaagtg atgtattcag tgacggcgga ggacatagcg     720
acgatggcgg gtgtccctat cgaatcttcc tacaaccagc tcaaagaagc ggccctgcgc     780
ctgaaacggc gggaagtccg gttaacccaa gagcccaatg gcaagggaa aagaccgagt     840 gtgatgatta ccggctgggt gcaaacaatc atctaccggg agggtgaggg ccgtgtagaa     900
ctcaggttca ccaaagacat gctgccgtac ctgacggaac tcaccaaaca gttcaccaaa     960
tacgccttgg ctgacgtggc caagatggac agcacccacg cgatcaggct ttacgagctg    1020
ctcatgcaat gggacagcat cggccagcgc gaaatagaaa ttgaccagct gcgaaagtgg    1080
tttcaactgg aaggccggta tccctcgatc aaggacttca agttgcgagt gcttgatcca    1140
```

```
gccgtgacgc agatcaacga gcacagcccg ctacaggtgg agtgggcgca gcgaaagacc    1200
gggcgcaagg tcacacatct gttgttcagt tttggaccga agaagcccgc caaggcggtg    1260
ggtaaggccc cagcgaagcg caaggccggg aagatttcag atgctgagat cgcgaaacag    1320
gctcgccctg gtgagacatg ggaagcggcc cgcgctcgac taacccagat gccgctggat    1380
ctggcctaga ggccgtggcc accacggccc ggcctgcctt tcaggctgcg caactgttgg    1440
gaagggcgat cggtgcgggc ctcttcgcta ttacgccagc tggcgaaagg gggatgtgct    1500
gcaaggcgat taagttgggt aacgccaggg ttttcccagt cacgacgttg taaaacgacg    1560
gccagtgaat tcgagctcgg tacccgggga tcctctagag tcgacctgca ggcatgcaag    1620
cttggcgtaa tcatggtcat agctgtttcc tgtgtgaaat tgttatccgc tcacaattcc    1680
acacaacata cgagccggaa gcataaagtg taaagcctgg ggtgcctaat gagtgagcta    1740
actcacatta attgcgttgc gctcactgcc cgctttccag tcgggaaacc tgtcgtgcca    1800
gctgcattaa tgaatcggcc aacgcgcggg gagaggcggt ttgcgtattg ggcgctcttc    1860
cgcttcctcg ctcactgact cgctgcgctc ggtcgttcgg ctgcggcgag cggtatcagc    1920
tcactcaaag gcggtaatac ggttatccac agaatcaggg gataacgcag gaaagaacat    1980
gtgagcaaaa ggccagcaaa aggccaggaa ccgtaaaaag gccgcgttgc tggcgttttt    2040
ccataggctc cgcccccctg acgagcatca caaaaatcga cgctcaagtc agaggtggcg    2100
aaacccgaca ggactataaa gataccaggc gtttccccct ggaagctccc tcgtgcgctc    2160
tcctgttccg accctgccgc ttaccggata cctgtccgcc tttctccctt cgggaagcgt    2220
ggcgctttct catagctcac gctgtaggta tctcagttcg gtgtaggtcg ttcgctccaa    2280
gctgggctgt gtgcacgaac cccccgttca gcccgaccgc tgcgccttat ccggtaacta    2340
tcgtcttgag tccaacccgg taagacacga cttatcgcca ctggcagcag ccactggtaa    2400
caggattagc agagcgaggt atgtaggcgg tgctacagag ttcttgaagt ggtggcctaa    2460
ctacggctac actagaagaa cagtatttgg tatctgcgct ctgctgaagc cagttacctt    2520
cggaaaaaga gttggtagct cttgatccgg caaacaaacc accgctggta gcggtggttt    2580
ttttgtttgc aagcagcaga ttacgcgcag aaaaaaagga tctcaagaag atcctttgat    2640
cttttctacg gggtctgacg ctcagtggaa cgaaaactca cgttaaggga ttttggtcat    2700
gagattatca aaaaggatct tcacctagat ccttttaaat taaaaatgaa gttttaaatc    2760
aatctaaagt atatatgagt aaacttggtc tgacagttac caatgcttaa tcagtgaggc    2820
acctatctca gcgatctgtc tatttcgttc atccatagtt gcctgactcc ccgtcgtgta    2880
gataactacg atacgggagg gcttaccatc tggccccagt gctgcaatga taccgcgaga    2940
cccacgctca ccggctccag atttatcagc aataaaccag ccagccggaa gggccgagcg    3000
cagaagtggt cctgcaactt tatccgcctc catccagtct attaattgtt gccgggaagc    3060
tagagtaagt agttcgccag ttaatagttt gcgcaacgtt gttgccattg ctacaggcat    3120
cgtggtgtca cgctcgtcgt ttggtatggc ttcattcagc tccggttccc aacgatcaag    3180
gcgagttaca tgatccccca tgttgtgcaa aaaagcggtt agctccttcg gtcctccgat    3240
cgttgtcaga agtaagttgg ccgcagtgtt atcactcatg gttatggcag cactgcataa    3300
ttctcttact gtcatgccat ccgtaagatg cttttctgtg actggtgagt actcaaccaa    3360
gtcattctga gaatagtgta tgcggcgacc gagttgctct tgcccggcgt caatacggga    3420
taataccgcg ccacatagca gaactttaaa agtgctcatc attggaaaac gttcttcggg    3480
gcgaaaactc tcaaggatct taccgctgtt gagatccagt tcgatgtaac ccactcgtgc    3540
```

```
acccaactga tcttcagcat cttttacttt caccagcgtt tctgggtgag caaaaacagg    3600
aaggcaaaat gccgcaaaaa agggaataag ggcgacacgg aaatgttgaa tactcatact    3660
cttccttttt caatattatt gaagcattta tcagggttat tgtctcatga gcggatacat    3720
atttgaatgt atttagaaaa ataaacaaat aggggttccg cgcacatttc cccgaaaagt    3780
gccacctgac gtctaagaaa ccattattat catgacatta acctataaaa ataggcgtat    3840
cacgaggccc tttcgtctcg cgcgtttcgg tgatgacggt gaaaacctct gacacatgca    3900
gctcccggag acggtcacag cttgtctgta agcggatgcc gggagcagac aagcccgtca    3960
gggcgcgtca gcgggtgttg gcgggtgtcg ggctggctt aactatgcgg catcagagca    4020
gattgtactg agagtgcacc atatgcggtg tgaaataccg cacagatgcg taaggagaaa    4080
ataccgcatc aggcggcaat ggcaacaacg ttgcgcaaac tattaactgg cgaactactt    4140
actctagctt cccggcaaca attaatagac tggatggagg cggataaagt tgcaggacca    4200
cttctgcgct cggcccttcc ggctggctgg tttattgctg ataaatctgg agccggtgag    4260
cgtggatctc gcggtatcat tgcagcactg gggccagatg gtaagccctc ccgtatcgta    4320
gttatctaca cgacggggag tcaggcaact atggatgaac gaaatagaca gatcgctgag    4380
ataggtgcct cactgattaa gcattggtaa ctgtcagacc aagtttactc atatatactt    4440
tagattgatt taaaacttca tttttaattt aaaaggatct aggtgaagat ccttttttgat    4500 aatctcatga ccaaaatccc ttaacgtgag ttttcgttcc actgagcgtc agacccc       4557

<210> SEQ ID NO 8
<211> LENGTH: 27
<212> TYPE: DNA
<213> ORGANISM: Artificial Sequence
<220> FEATURE:
<223> OTHER INFORMATION: accA forward primer

<400> SEQUENCE: 8
tctagacgac ggaagcctat gaacccg                                        27

<210> SEQ ID NO 9
<211> LENGTH: 27
<212> TYPE: DNA
<213> ORGANISM: Artificial Sequence
<220> FEATURE:
<223> OTHER INFORMATION: accA reverse primer

<400> SEQUENCE: 9
ggatccttac ggcgcgccgt agctcat                                        27

<210> SEQ ID NO 10
<211> LENGTH: 29
<212> TYPE: DNA
<213> ORGANISM: Artificial Sequence
<220> FEATURE:
<223> OTHER INFORMATION: fabD forward primer

<400> SEQUENCE: 10
ggtacccaag ggacctattc aatgtctgc                                      29

<210> SEQ ID NO 11
<211> LENGTH: 29
<212> TYPE: DNA
<213> ORGANISM: Artificial Sequence
<220> FEATURE:
<223> OTHER INFORMATION: fabD reverse primer

<400> SEQUENCE: 11
```

```
gagctcttct ctcctttctc tctctcagg                                    29

<210> SEQ ID NO 12
<211> LENGTH: 30
<212> TYPE: DNA
<213> ORGANISM: Artificial Sequence
<220> FEATURE:
<223> OTHER INFORMATION: 3.1.2.14 forward primer

<400> SEQUENCE: 12
gagctcggag agtattatgg gattaagtta                                   30

<210> SEQ ID NO 13
<211> LENGTH: 29
<212> TYPE: DNA
<213> ORGANISM: Artificial Sequence
<220> FEATURE:
<223> OTHER INFORMATION: 3.1.2.14 reverse primer

<400> SEQUENCE: 13
gaattcctag tctatctcgc tttctgttt                                    29
```

PSEUDOMONAS AERUGINOSA STRAIN DEVELOPED FOR IMPROVING FATTY ACID CONTENT, AND METHOD OF MANUFACTURING THE SAME

This application is a 371 of PCT/KR11/01554 filed Mar. 7, 2011, which claims foreign priority to the following applications from Republic of Korea: 10-2010-0037546, filed Apr. 22, 2010 and 10-2011-0014270 filed Feb. 17, 2011.

TECHNICAL FIELD

The present invention relates to a novel recombinant *Pseudomonas aeruginosa* strain and a method for preparing the same. More particularly, the present invention relates to a novel *Pseudomonas aeruginosa* strain transformed with a gene associated with fatty acid biosynthesis and a method for preparing the same.

BACKGROUND ART

The burning of fossil fuels produces a tremendous amount of greenhouse gases and wastes that contribute to global warming, bringing a serious environmental crisis to bear upon mankind. Given this situation, there is a pressing need for the development of new, environmentally friendly bioprocesses that uses biomass as fuel, as an alternative to the chemical processes based on fossil fuels to minimize the production of detrimental wastes and the consumption of non-renewable energy. In recent years, there has been a great increase in interest in various bioenergy sources including bioethanol, biodiesel, biogas, and butanol. Some of the kinds of bioenergy sources can be used as fuels for electricity production or transportation, but have drawbacks because of their applicability and production. Now, attention is turning to renewable hydrocarbon compounds, with a concomitant increase of interest in recombinant strains capable of producing long chain fatty acids as their products.

*Pseudomonas aeruginosa* was first obtained in a pure culture by Gessard in 1882 from cutaneous wounds which had a blue green discoloration. This bacterial species is widely found in nature and frequently isolated from pus, phlegm, excreta, urine, bile, uterine secretions, blood, and spinal fluid. *Pseudomonas aeruginosa* is a Gram-negative, rod-shaped bacterium that forms a mucous layer composed of extracellular polysaccharides, similar to capsules. This bacterium has great adaptability to any environment, with very simple auxotrophic requirements for growth. *Streptococcus pyogenes* is a spherical, Gram-positive bacterium that is the cause of many important human diseases, including pneumonia, pharyngitis, acute nephritis, and toxic shock syndrome.

A fatty acid is a monovalent carboxylic acid (—COOH) with a long hydrocarbon chain. Fatty acids are so named because they are produced by the hydrolysis of lipids. In the backbone of a fatty acid, hydrogen atoms are linked to each carbon atom, with a carboxyl group at one end. Fatty acids are degraded or synthesized in vivo through the fatty acid cycle. Most naturally occurring fatty acids have a chain composed of an even number of carbon atoms because the carbons are cleaved from or added to the hydrocarbon chain of the fatty acid in two-carbon atom groups.

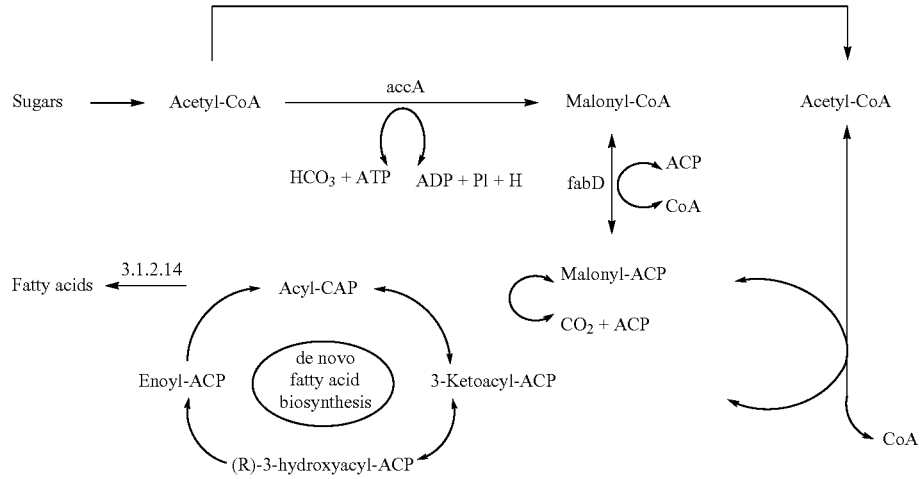

In microorganisms, the biosynthesis of fatty acids from sugar starts with acetyl-CoA. Then, the chain is lengthened with the addition of a two-carbon atom unit per cycle to the growing hydrocarbon chain. In the cytoplasm, acetyl-CoA is carboxylated into malonyl-CoA which acts as an important mediator in fatty acid biosynthesis. This irreversible carboxylation is catalyzed by acetyl-CoA carboxylase. The enzyme is composed of three enzymatic subunits and requires biotin and $Mn^{2+}$ as a cofactor with the supply of ATP during the carboxylation. Two of the three carbon atoms in the malonyl moiety of malonyl-CoA are added to the growing fatty acid chain per cycle of the biosynthesis. Like the production of malonyl-CoA, this reaction is carried out in the cytoplasm by a multi-enzyme protein which is not bound to the membrane.

This multi-enzyme protein composed of individual functional enzymes is named fatty acid synthase. The acyl carrier protein (ACP) is an important component of the fatty acid synthase, with the growing chain bound thereto during synthesis.

Incessant trials and effort have been made to overexpress fatty acids in microbes using microbial fatty acid metabolism pathways. Information about the metabolism of *E. coli* is much more abundant, compared to other microbial organisms. In fact, *E. coli* is widely used for the production of recombinant proteins because all of its genes have been identified and analyzed. However, not much research has been conducted into the effect of the expression of exogenous genes from other species in *Pseudomonas aeruginosa*.

Many studies have been done into improving the production of fatty acids by the introduction of plant genes into *E. coli*, but genes from other microbial species have not been studied very much for improving fatty acid production, as is done the case for the present invention.

Thus, the present inventors introduced a gene from *Pseudomonas*, which is rich in lipids including fatty acids, and a gene from a Gram-positive species, which is novel to *Pseudomonas*, into *Pseudomonas*, so as to produce fatty acids at greater efficiency.

In the present invention, gene manipulation was carried out, on the basis of the complete understanding of the biological metabolism networks of *Pseudomonas aeruginosa*, to create a novel recombinant species which can produce a desired metabolite with high efficiency in an early step of the fatty acid biosynthesis pathway.

Culminating in the present invention, intensive and thorough research into the stable and effective production of fatty acids by gene manipulation, conducted by the present inventors, resulted in the finding that when transformed with a nucleotide sequence coding for acetyl-CoA carboxylase carboxytransferase subunit alpha of *Pseudomonas aeruginosa* and/or a nucleotide sequence coding for malonyl-CoA-[acyl-carrier-protein] transacylase, and a nucleotide sequence coding for acyl-acyl carrier protein thioesterase of *Streptococcus pyogenes*, *Pseudomonas aeruginosa* can overexpress the enzymes involved in the fatty acid biosynthesis pathway to activate the pathway, thus producing fatty acids in high yield.

DISCLOSURE

Technical Problem

It is an object of the present invention to provide a novel *Pseudomonas aeruginosa* strain capable of producing a fatty acid in high yield.

It is another object of the present invention to provide a method for preparing the *Pseudomonas aeruginosa* strain.

It is a further object of the present invention to provide a method for the mass production of lipids or fatty acids using the *Pseudomonas aeruginosa* strain.

Technical Solution

In accordance with an aspect thereof, the present invention provides a *Pseudomonas aeruginosa* strain, capable of producing a fatty acid in high yield, being transformed with an expression vector carrying a nucleotide sequence coding for acyl-acyl carrier protein thioesterase of *Streptococcus pyogenes*.

In accordance with another aspect thereof, the present invention provides a *Pseudomonas aeruginosa* strain, capable of producing a fatty acid in high yield, being transformed with an expression vector carrying a nucleotide coding for acetyl-CoA carboxylase carboxytransferase subunit alpha of *Pseudomonas aeruginosa* and a nucleotide sequence coding for acyl-acyl carrier protein thioesterase of *Streptococcus pyogenes*.

In accordance with a further aspect thereof, the present invention provides a *Pseudomonas aeruginosa* strain, capable of producing a fatty acid in high yield, being transformed with an expression vector carrying a nucleotide sequence coding for malonyl-CoA-[acyl-carrier-protein] transacylase of *Pseudomonas aeruginosa* and a nucleotide sequence coding for acyl-acyl carrier protein thioesterase of *Streptococcus pyogenes*.

In accordance with still a further aspect thereof, the present invention provides a *Pseudomonas aeruginosa* strain, capable of producing a fatty acid in high yield, being transformed with an expression vector carrying a nucleotide sequence coding for acetyl-CoA carboxylase carboxytransferase subunit alpha, a nucleotide sequence coding for malonyl-CoA-[acyl-carrier-protein] transacylase, both derived from *Pseudomonas aeruginosa*, and a nucleotide sequence coding for an acyl-acyl carrier protein thioesterase of *Streptococcus pyogenes*.

In accordance with still another aspect thereof, the present invention provides a method for preparing *Pseudomonas aeruginosa* capable of producing a fatty acid in high yield, comprising: i) inserting a nucleotide sequence coding for an acyl-acyl carrier protein thioesterase of *Streptococcus pyogenes* into an expression vector; and ii) transforming the expression vector of step i) into *Pseudomonas aeruginosa*.

In accordance with yet another aspect thereof, the present invention provides a method for preparing *Pseudomonas aeruginosa* capable of producing a fatty acid in high yield, comprising: i) inserting into an expression vector either or both of a nucleotide coding for acetyl-CoA carboxylase carboxytransferase subunit alpha and a nucleotide sequence coding for malonyl-CoA-[acyl-carrier-protein] transacylase, and a nucleotide sequence coding for an acyl-acyl carrier protein thioesterase of *Streptococcus pyogenes*; and ii) transforming the expression vector of step i) into *Pseudomonas aeruginosa*.

In accordance with yet a further aspect thereof, the present invention provides a method for producing a fatty acid, comprising: i) culturing the *Pseudomonas aeruginosa* of any one of claims 1 to 4 to allow a fatty acid to be synthesized in the cell; and ii) recovering the fatty acid synthesized in step i).

Advantageous Effects

Transformed with an expression vector carrying enzymes involved in the early stage of the fatty acid biosynthesis pathway, the *Pseudomonas aeruginosa* of the present invention can overexpress the enzymes and thus can produce lipids and fatty acids in high yield. That is, the present invention allows enzymes involved in the fatty acid biosynthesis from glucose to be overexpressed and modifies the metabolism flow by introducing exogenous genes, thus producing a fatty acid in high yield. Therefore, it is expected that the present invention will be used in the mass production of fatty acids, useful as a bioenergy source, in an environmentally friendly and economically beneficial manner.

DESCRIPTION OF DRAWINGS

FIG. 1 is a schematic view of the fatty acid biosynthesis (FAS) pathway of *Pseudomonas aeruginosa* ranging from glucose to fatty acids.

FIG. 2 is a schematic view of the genetic map of the *Escherichia coli-Pseudomonas* shuttle vector pUCP19.

Figure 3:
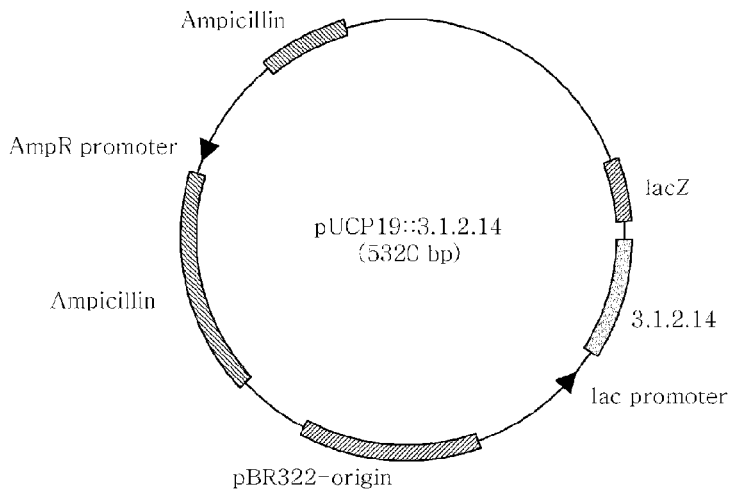
FIG. 3 is a schematic view of the genetic map of the *Escherichia coli-Pseudomonas* shuttle vector pUCP19 transformed with the acyl-acyl carrier protein thioesterase (E.C.3.1.2.14) gene (it is named pJS04 in the present invention).
Figure 4:
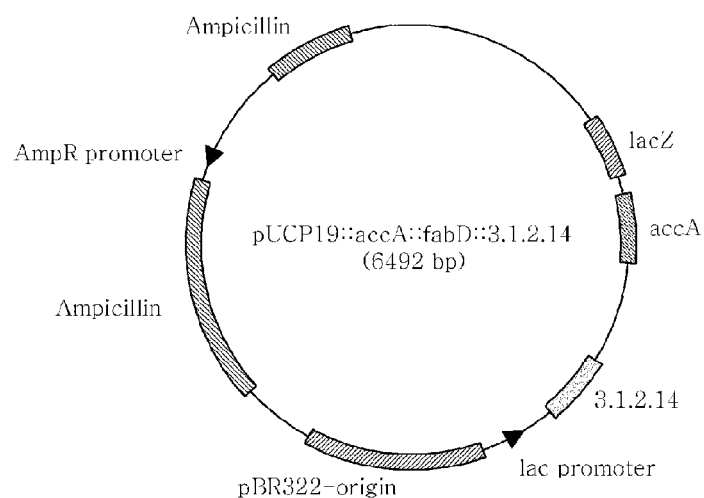
FIG. 4 is a schematic view of the genetic map of the *Escherichia coli-Pseudomonas* shuttle vector pUCP19 transformed with the accA gene and the acyl-acyl carrier protein thioesterase (E.C.3.1.2.14) gene (it is named pJS05 in the present invention).

(A) Genes in the recombinant vector of FIG. 3 (lane 1: size marker, lane 2: accA, lane 3: 3.1.2.14); and (B) Genes in the recombinant vector of FIG. 4 (lane 1: size marker, lane 2: fabD, lane 3: 3.1.2.14, lane 4: fabD, lane 5: 3.1.2.14).

Figure 8:
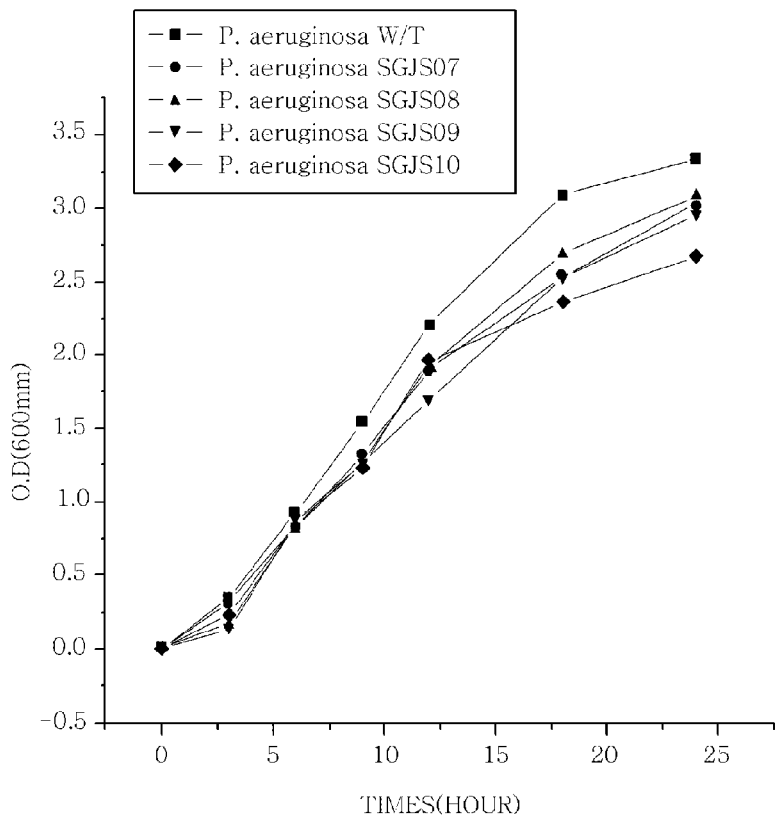

FIG. 8 is a graph showing the growth of the recombinant *Pseudomonas aeruginosa* strains, and the wild-type.

Figure 9:
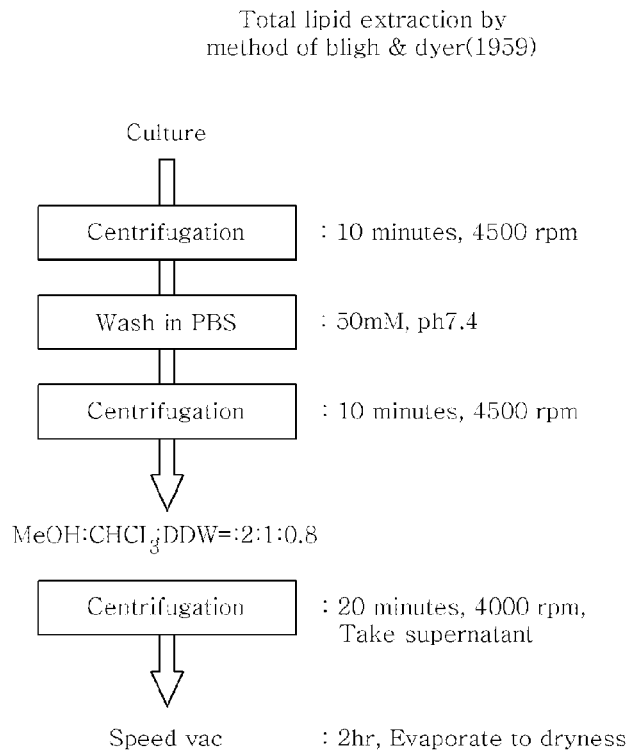

FIG. 9 is a schematic view illustrating the extraction of lipids from a culture of *Pseudomonas aeruginosa*.

Figure 10:
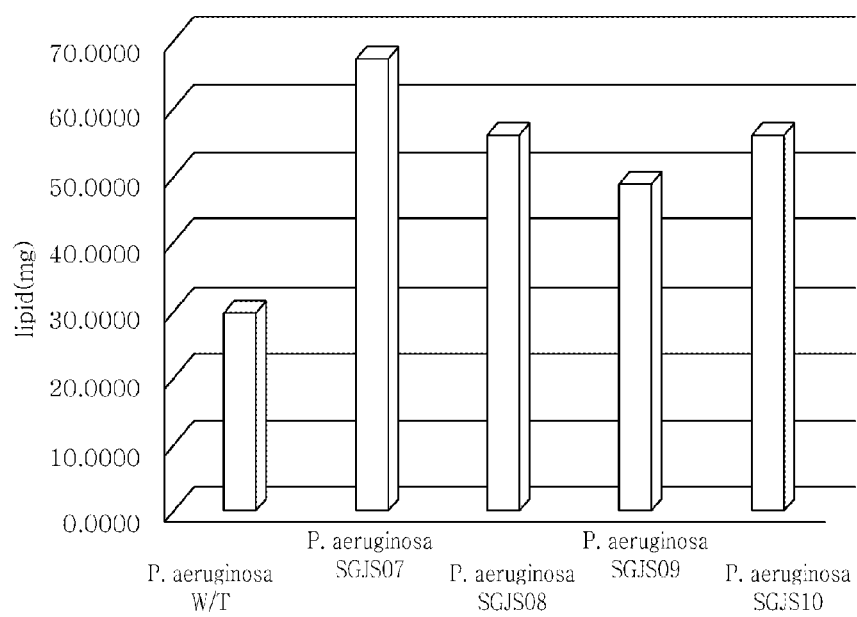

FIG. 10 is a graph of intracellular levels of lipids extracted from the recombinant *Pseudomonas aeruginosa* strains of the present invention and the wild-type after culture for 24 hrs.

Figure 11:
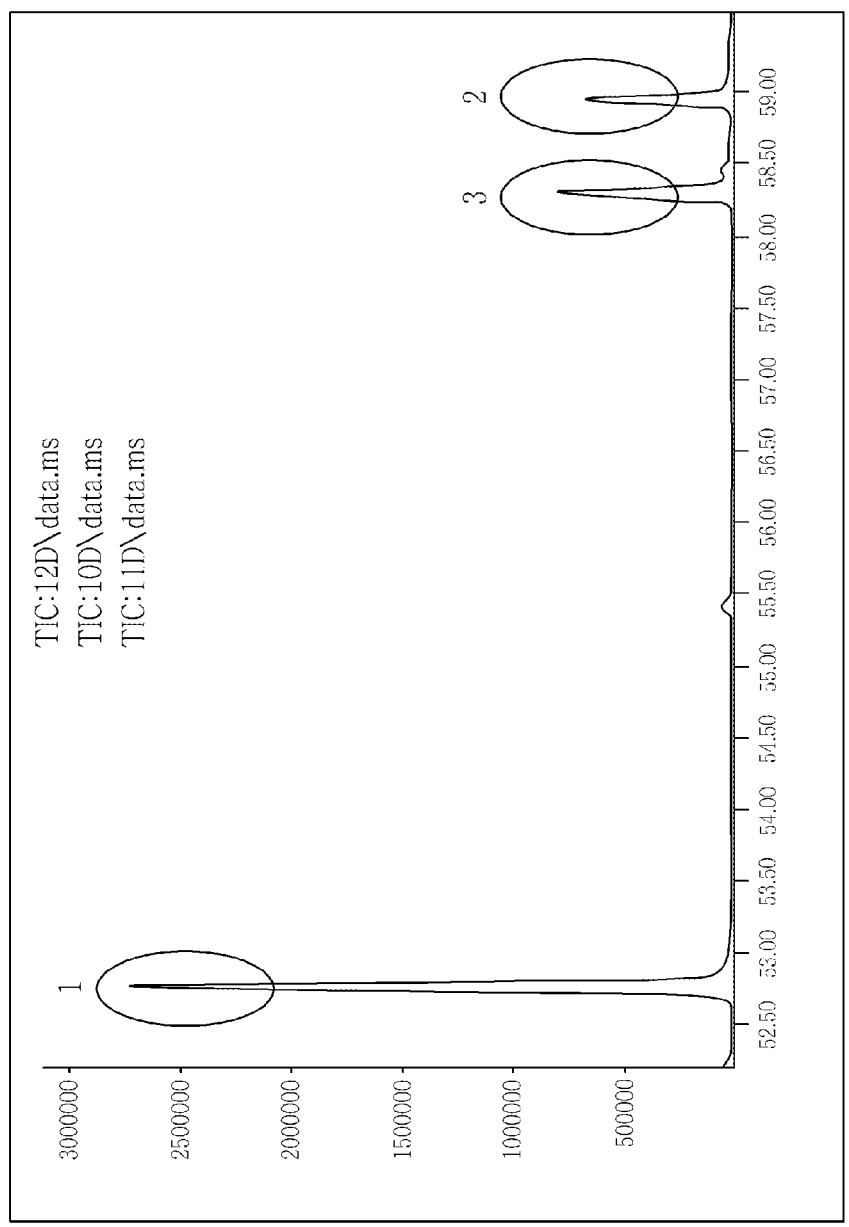

FIG. 11 is a GC chromatogram showing the intracellular levels of fatty acids extracted from the recombinant *Pseudomonas aeruginosa* strain of the present invention after culture for 24 hrs.

Figure 12:
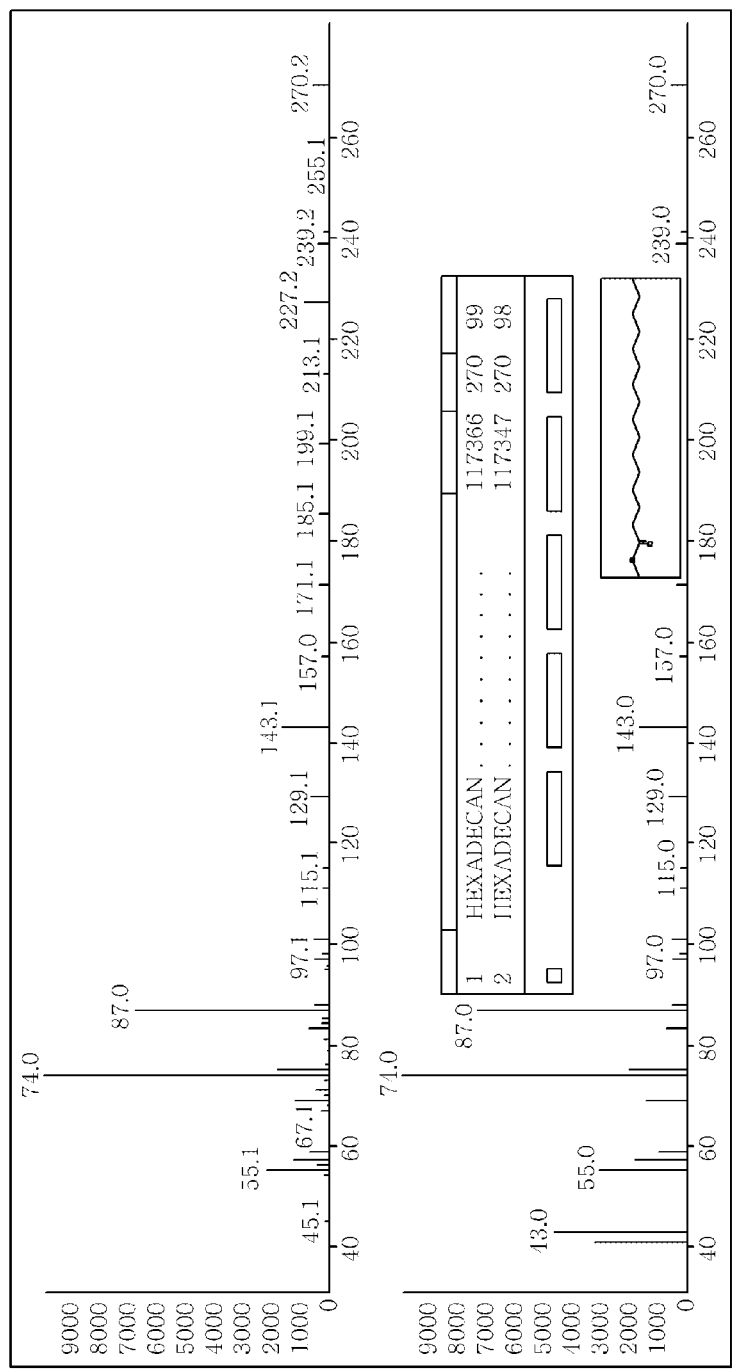
Figure 13:
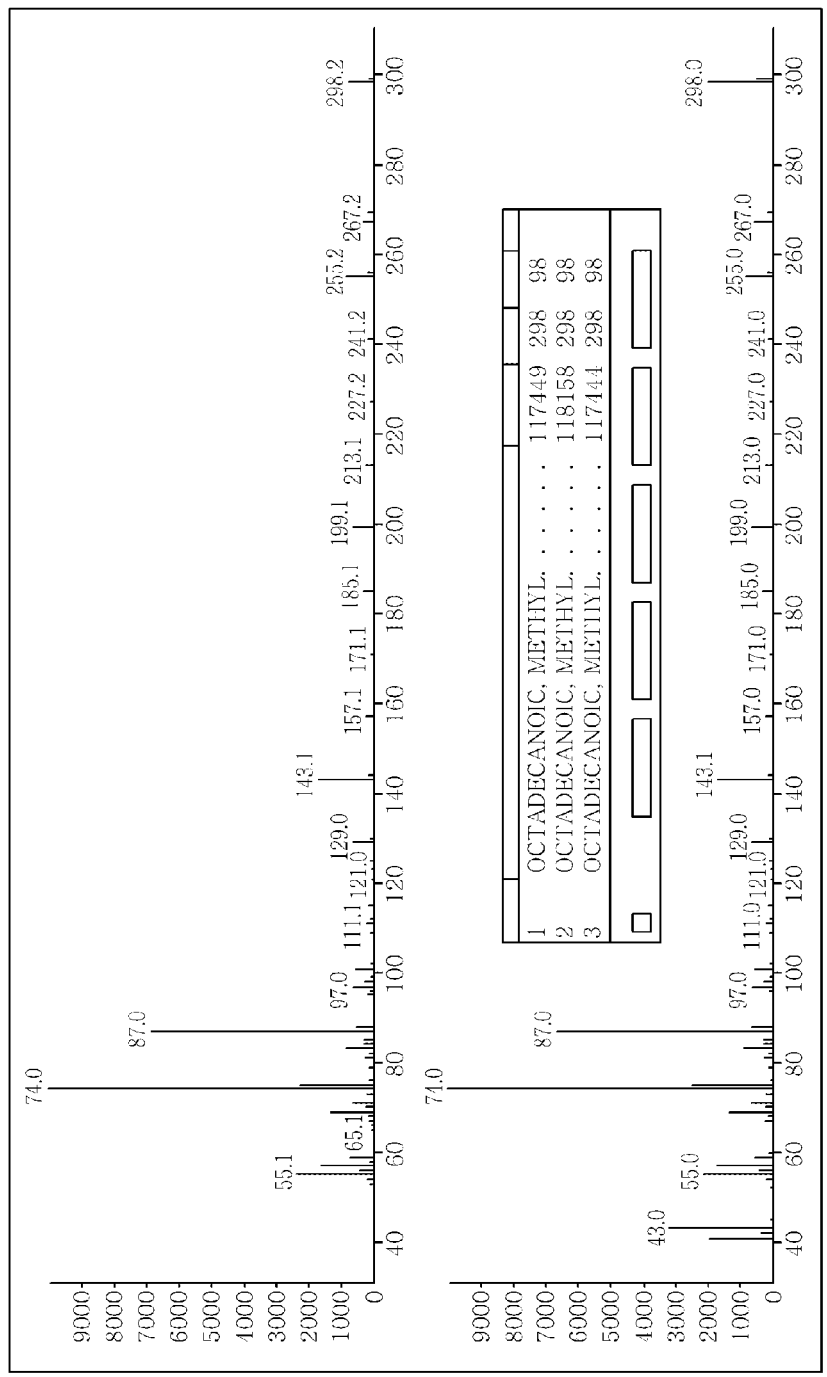
Figure 14:
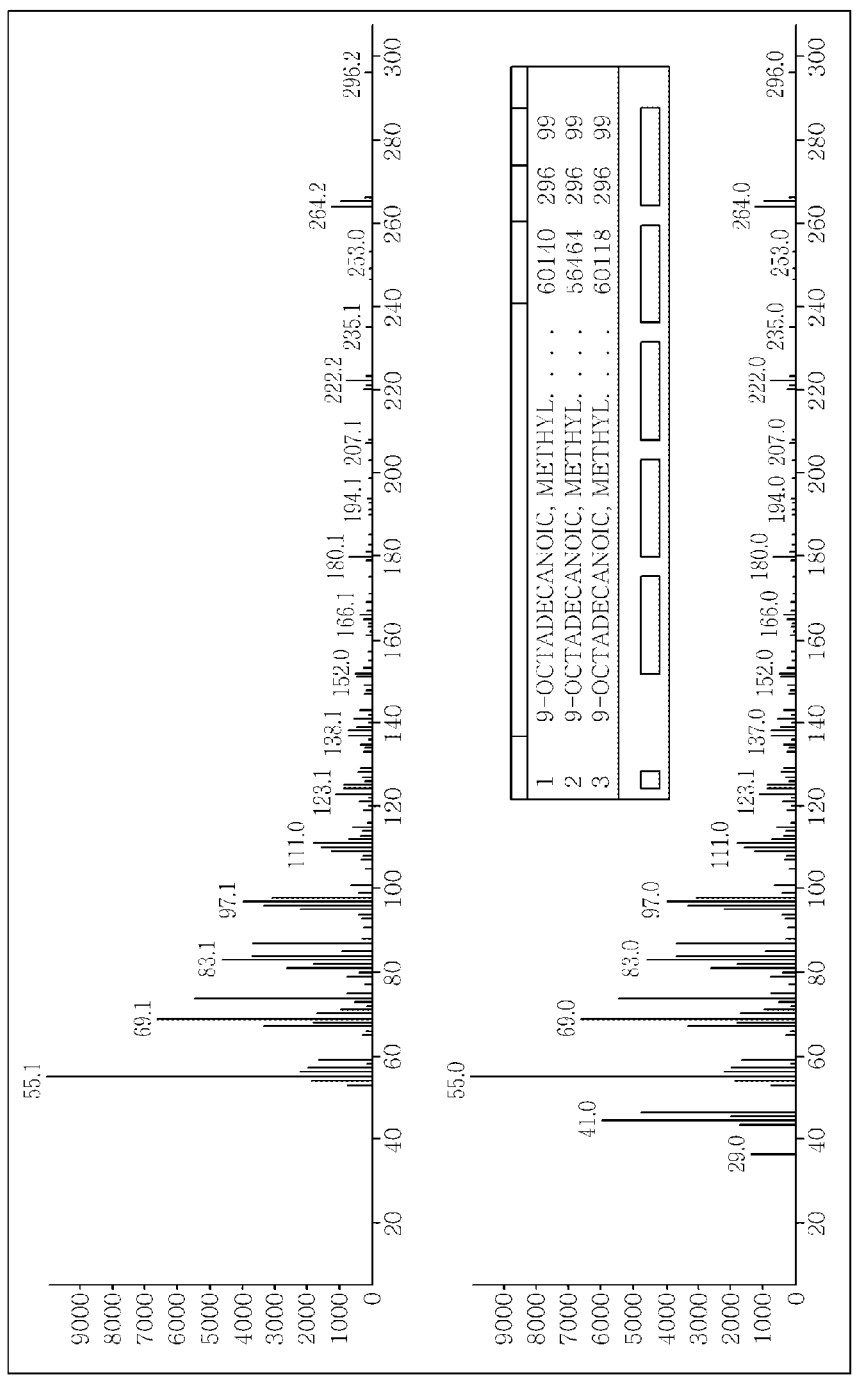

FIGS. 12 to 14 show fatty acid components in the recombinant *Pseudomonas aeruginosa* strains as measured by GC/MS (Gas chromatography-mass spectrometry):

FIG. 12 shows GC/MS spectra of C-16 hexadecanoic acid.

FIG. 13 shows GC/MS spectra of C-18 octadecanoic acid.

FIG. 14 shows GC/MS spectra of C-18 9-octadecenoic acid.

Figure 15:
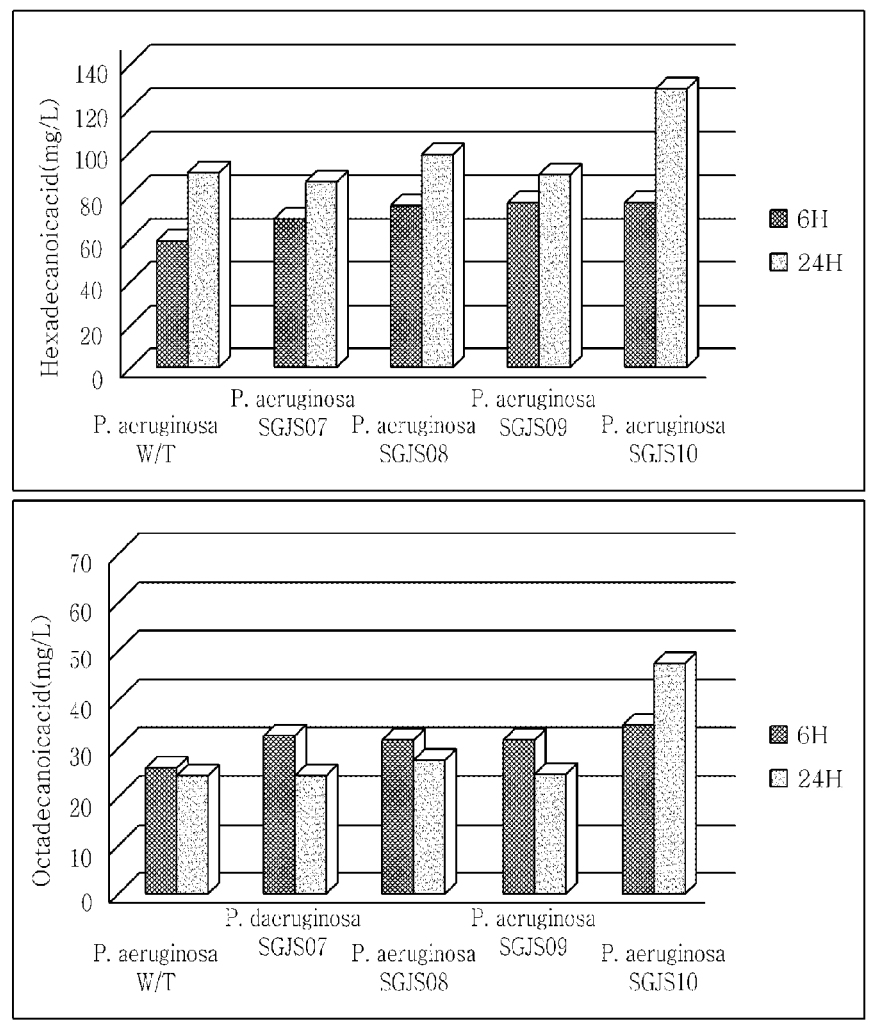

FIG. 15 shows levels of hexadecanoic acid and octadecanoic acid in the recombinant *Pseudomonas aeruginosa* strains of the present invention and the wild-type after IPTG induction for 6 and 24 hrs.

MODE FOR INVENTION

Below, a detailed description will be given of the present invention.

In accordance with one aspect thereof, the present invention envisages a *Pseudomonas aeruginosa* strain in which proteins involved in the fatty acid biosynthesis pathway starting from glucose are overexpressed and/or the pathway is modified by the insertion of an exogenous gene, whereby fatty acids can be produced in high yield.

Accordingly, the present invention addresses a *Pseudomonas aeruginosa* strain, capable of producing a fatty acid in high yield, being transformed with an expression vector carrying a nucleotide sequence coding for acyl-acyl carrier protein thioesterase of *Streptococcus pyogenes*.

In addition, the present invention addresses a *Pseudomonas aeruginosa* strain, capable of producing a fatty acid in high yield, being transformed with an expression vector carrying a nucleotide coding for acetyl-CoA carboxylase carboxytransferase subunit alpha of *Pseudomonas aeruginosa* and a nucleotide sequence coding for acyl-acyl carrier protein thioesterase of *Streptococcus pyogenes*.

Also, the present invention addresses a *Pseudomonas aeruginosa* strain, capable of producing a fatty acid in high yield, being transformed with an expression vector carrying a nucleotide sequence coding for malonyl-CoA-[acyl-carrier-protein] transacylase of *Pseudomonas aeruginosa* and a nucleotide sequence coding for acyl-acyl carrier protein thioesterase of *Streptococcus pyogenes*.

Further, the present invention addresses a *Pseudomonas aeruginosa* strain, capable of producing a fatty acid in high yield, being transformed with an expression vector carrying a nucleotide sequence coding for acetyl-CoA carboxylase carboxytransferase subunit alpha, a nucleotide sequence coding for malonyl-CoA-[acyl-carrier-protein] transacylase, both derived from *Pseudomonas aeruginosa*, and a nucleotide sequence coding for acyl-acyl carrier protein thioesterase of *Streptococcus pyogenes*.

In one embodiment of the present invention, a recombinant *Pseudomonas aeruginosa* strain is prepared by transforming wild-type *Pseudomonas aeruginosa* with an expression vector carrying a *Streptococcus pyogenes*-derived nucleotide sequence coding for acyl-acyl carrier protein thioesterase. In another embodiment of the present invention, a recombinant *Pseudomonas aeruginosa* strain is prepared by transforming wild-type *Pseudomonas aeruginosa* with an expression vector carrying a *Pseudomonas aeruginosa*-derived nucleotide coding for acetyl-CoA carboxylase carboxytransferase subunit alpha and/or a *Pseudomonas aeruginosa*-derived nucleotide sequence coding for malonyl-CoA-[acyl-carrier-protein] transacylase, and a *Streptococcus pyogenes*-derived nucleotide sequence coding for acyl-acyl carrier protein thioesterase.

To examine the ability of the recombinant *Pseudomonas aeruginosa* strains of the present invention to produce lipids, lipids were extracted from cultures of the recombinant strains and quantitatively analyzed. Higher lipid levels were detected in all the recombinant strains than the wild-type *Pseudomonas aeruginosa* (FIG. 10).

Also, an examination was made to see whether intracellular fatty acid levels were enhanced by the recombinant *Pseudomonas aeruginosa* strains of the present invention. Quantitative analysis of fatty acids extracted from cultures of the cells showed that all the recombinant *Pseudomonas aeruginosa* strains of the present invention produced higher levels of fatty acids, particularly, hexadecanoic acid, octadecanoic acid and 9-octadecenoic acid than did the wild-type *Pseudomonas aeruginosa* (FIGS. 11 to 13).

Therefore, as will be demonstrated in the following Example section, the *Pseudomonas aeruginosa* strains transformed with an expression vectors carrying the genes involved in the fatty acid biosynthesis pathway in accordance with the present invention can not only promote the production of lipids, but can increase the content of fatty acids themselves therein, and thus can be useful for the mass production of fatty acids.

In the present invention, acetyl-CoA carboxylase carboxytransferase is the enzyme that catalyzes the carboxylation of acetyl-CoA to malonyl-CoA and forms a tetramer composed of two alpha and two beta subunits. One of the subunits corresponds to the acetyl-CoA carboxylase carboxytransferase subunit alpha, preferably encoded by the accA gene.

Preferably, the acetyl-CoA carboxylase carboxytransferase subunit alpha is derived from *Pseudomonas aeruginosa*. In a preferred embodiment, the acetyl-CoA carboxylase carboxytransferase subunit alpha has the amino acid sequence of SEQ ID NO: 1, encoded by the nucleotide sequence of SEQ ID NO: 2.

In the present invention, malonyl-CoA-[acyl-carrier protein] transacylase refers to the enzyme that catalyses the conversion of malonyl-CoA to malonyl-ACP and is preferably encoded by the fabD gene.

Preferably, the malonyl-CoA-[acyl-carrier protein] transacylase is derived from *Pseudomonas aeruginosa*. In one preferred embodiment, the malonyl-CoA-[acyl-carrier protein] transacylase has the amino acid sequence of SEQ ID NO: 3, encoded by the nucleotide sequence of SEQ ID NO: 4.

In the present invention, the acyl-acyl carrier protein thioesterase refers to an enzyme which is indispensible to the biological production of long-chain fatty acids through the fatty acid biosynthesis pathway and is involved in the extension of fatty acid chains from malonyl-ACP. This enzyme is preferably encoded by the 3.1.2.14 gene and is not found in wild-type *E. coli*.

The acyl-acyl carrier protein thioesterase expressed from the expression vector according to the present invention is preferably *Streptococcus* derived. More preferably, the acyl-acyl carrier protein thioesterase has the amino acid sequence of SEQ ID NO: 5, encoded by the nucleotide sequence of SEQ ID NO: 6.

It should be understood by those skilled in the art that nucleotide sequences useful in the present invention are not limited to the above-mentioned nucleotide sequences, but may include nucleotide sequences that have a substantial identity with the above-mentioned nucleotide sequences. The substantial identity is at least 80%, more preferably at least 90%, and most preferably at least 95% as analyzed by typically used algorithm from most probable alignments of nucleotide sequences. Alignment methods for sequence comparison are well known in the art. With regard to various alignment methods and algorithms, reference may be made to Smith and Waterman, *Adv. Appl. Math.* 2:482(1981); Needleman and Wunsch, *J. Mol. Bio.* 48:443(1970); Pearson and Lipman, *Methods in Mol. Biol.* 24: 307-31(1988); Higgins and Sharp, *Gene* 73:237-44(1988); Higgins and Sharp, *CABIOS* 5:151-3(1989); Corpet et al., *Nuc. Acids Res.* 16:10881-90(1988); Huang et al., *Comp. Appl. BioSci.* 8:155-65(1992) and Pearson et al., *Meth. Mol. Biol.* 24:307-31 (1994). The Basic Local Alignment Search Tool (BLAST) program (Altschul et al., *J. Mol. Biol.* 215:403-10(1990)), developed by the U. S. National Center for Biological Information (NCBI), can be accessed for free over the web www.ncbi.nlm.nih.gov/BLAST/, hosted by the NCBI, and can be used in association with a sequence analysis program, such as blastp, blasm, blastx, tblastn and tblastx, on the web.

In the present invention, the expression vector refers to a linear or circular DNA molecule in which a gene encoding a polypeptide of interest is operatively linked to a regulatory element for transcription. The regulatory element comprises a promoter and a termination codon. In addition, the expression vector contains at least one replication origin, at least one selection marker, and a polyadenylation signal. Also, it may be preferably derived from either a plasmid or a viral DNA, or may contain both. The vector system of the present invention may be constructed using various methods well known in the art, and details thereof are described more fully in Sambrook et al., Molecular Cloning, A Laboratory Manual, Cold Spring Harbor Laboratory Press (2001), which is herein incorporated by reference.

In an expression vector, a nucleotide coding for acetyl-CoA carboxylase carboxytransferase subunit alpha, a nucleotide sequence coding for malonyl-CoA-[acyl-carrier-protein] transacylase and/or a *Streptococcus pyogenes*-derived nucleotide sequence coding for acyl-acyl carrier protein thioesterase are operably linked to an expression control sequence. As used herein, the term "operably linked" refers to the association of nucleic acid sequences on a single nucleic acid fragment so that the function of one is regulated by the other. The term "expression control sequence," as used herein, refers to a DNA sequence that regulates the expression of a nucleotide sequence operably linked thereto in a certain host cell. In addition, the expression control sequence may comprises a promoter for initiating transcription, an operator for regulating transcription, a sequence coding for a suitable mRNA ribosome binding site, and sequences for regulating the termination of transcription and translation.

In one embodiment of the present invention, the expression vector may carry a full-length nucleotide sequence of the accA gene, a full-length nucleotide sequence of the fabD gene, and/or a full-length nucleotide sequence of the 3.1.2.14 gene, but the present invention is not limited thereby. Preferably, the cording region of each of the accA gene, the fabD gene and the 3.1.2.14 gene was designed to have the minimal length required of a nucleotide sequence comprising only indispensible elements, to reduce the metabolic burden placed on the host cell.

In another embodiment of the present invention, the expression vector may further carry a lad gene. The lacI gene can regulate the promoter irrespective of the presence of a gene encoding an Lac suppressor. In this case, the expression of accA, fabD and/or 3.1.2.14 genes may be induced by IPTG (isopropyl-βdthiogalactopyranoside).

The expression vector carries a structural gene, and may be a plasmid, a viral vector or a mediator which allows the structural gene to be expressed in a host cell. Preferred is a plasmid vector. So long as it can replicate and allow gene expression in *Pseudomonas aeruginosa*, any plasmid may be used. Preferable is the *E. coli-Pseudomonas* shuttle vector pUCP19(ATCC 87110; Schweizer, 1991). The *E. coli-Pseudomonas* shuttle vector pUCP19 is derived from pUC19 and a two-host-range plasmid vector (refer to Schweizer H. P., *Escherichia-Pseudomonas* shuttle vectors derived from pUC18/19, Gene, 97(1):109-121(1991)).

In the present invention, the transformation is preferably carried out using a $CaCl_2$ method (Cohen, S. N. et al., Proc. Natl. Acad. Sci. USA, 9:2110-2114(1973)), a Hanahan method (Cohen, S. N. et al., Proc. Natl. Acad. Sci. USA, 9:2110-2114(1973); and Hanahan, D., J. Mol. Biol., 166:557-580(1983)) or electroporation (Dower, W. J. et al., Nucleic. Acids Res., 16:6127-6145(1988)). Preferred is electroporation in terms of the stable and efficient construction of transformants.

As a host cell used in the present invention, *Pseudomonas aeruginosa* is a microorganism having an intrinsic fatty acid biosynthesis pathway and can activate the pathway effectively and reproducibly when it is transformed to overexpress the enzymes involved in the fatty acid biosynthesis pathway. As such, preferable is a wild-type species that is industrially applicable and has excellent functions. More preferred is *Pseudomonas aeruginosa* PA14.

In accordance with another aspect thereof, the present invention addresses a method for preparing the *Pseudomonas aeruginosa* strain capable of producing a fatty acid in high yield.

This method comprises:

i) inserting a nucleotide sequence coding for an acyl-acyl carrier protein thioesterase of *Streptococcus pyogenes* into an expression vector; and ii) transforming the expression vector of step i) into *Pseudomonas aeruginosa*.

Also contemplated in accordance with one embodiment of the present invention is a method for preparing a *Pseudomonas aeruginosa* strain capable of producing a fatty acid in high yield, comprising:

i) inserting into an expression vector either or both a nucleotide coding for acetyl-CoA carboxylase carboxytransferase subunit alpha and a nucleotide sequence coding for malonyl-CoA-[acyl-carrier-protein] transacylase, and a nucleotide sequence coding for an acyl-acyl carrier protein thioesterase of *Streptococcus pyogenes*; and ii) transforming the expression vector of step i) into *Pseudomonas aeruginosa*.

The expression vector useful in the methods of the present invention carries a structural gene, and may be a plasmid, a viral vector or a mediator which allows the structural gene to be expressed in a host cell. Preferred is a plasmid vector. So long as it can replicate and allow gene expression in *Pseudomonas aeruginosa*, any plasmid may be used. Preferable is the *E. coli-Pseudomonas* shuttle vector pUCP19 (ATCC 87110; Schweizer, 1991), but the present invention is not limited thereto.

In the methods of the present invention, the transformation is preferably carried out using a $CaCl_2$ method (Cohen, S. N. et al., Proc. Natl. Acad. Sci. USA, 9:2110-2114(1973)), a Hanahan method (Cohen, S. N. et al., Proc. Natl. Acad. Sci. USA, 9:2110-2114(1973); and Hanahan, D., J. Mol. Biol., 166:557-580(1983)) or electroporation (Dower, W. J. et al., Nucleic. Acids Res., 16:6127-6145(1988)). Preferred is electroporation, but the present invention is not limited thereto.

In accordance with a further aspect thereof, the present invention addresses a method for the mass production of a fatty acid using the recombinant *Pseudomonas aeruginosa* strain capable of producing a fatty acid in high yield.

The method comprises:

i) culturing the recombinant *Pseudomonas aeruginosa* strain of the present invention to allow a fatty acid to be synthesized; and ii) recovering the fatty acid synthesized in step i).

In the method of the present invention, the *Pseudomonas aeruginosa* transformant of the present invention may be cultured using a typical method well known in the art. Preferably, the bacteria may be preferably cultured in LB broth at 37° C. In addition, the culturing step may be carried out in the presence of the expression inducer IPTG.

In the method of the present invention, the recovery of the fatty acid synthesized in the *Pseudomonas aeruginosa* transformant may be implemented using typical separation or purification well known in the art (refer to B. Aurousseau et al., Journal of the American Oil Chemists' Society, 57(3): 1558-9331(1980); Frank C. Magne et al., Journal of the American Oil Chemists' Society, 34(3):127-129(1957)). Thus, when the *Pseudomonas aeruginosa* transformant is cultured to overexpress the enzymes involved in the fatty acid biosynthesis pathway, a fatty acid useful as a beneficial energy source can be readily obtained.

A better understanding of the present invention may be obtained through the following examples which are set forth to illustrate, but are not to be construed as limiting the present invention.

Example 1

Construction of Recombinant Plasmids Carrying accA and fabD Genes and Carrying 3.1.2.14 Gene Using Polymerase Chain Reaction (PCR)

Nucleotide sequences of accA and fabD (GenBank, NCBI), which encode enzymes responsible for the production of malonyl-CoA and malonyl-CoA:ACP, respectively, were amplified by PCR (DaKaRa, Korea) using primers with the genomic DNA of *Pseudomonas aeruginosa* PAO1 (KCCM) serving as a template. Separately, PCR was performed on the genomic DNA of *Streptococcus pyogenes* MGAS10270 (ATCC) in the presence of primers suitable for amplifying a gene encoding acyl-acyl carrier protein thioesterase (E.C 3.1.2.14) (GenBank, NCBI), which is new to *Pseudomonas aeruginosa* (Tables 1 and 2).

TABLE 1

| Gene | Enzyme |
|---|---|
| accA | acetyl-CoA carboxylase, carboxytransferase, alpha subunit |
| fabD | malonyl-CoA-[acyl-carrier-protein]transacylase |
| 3.1.2.14 | acyl-acyl carrier protein thioesterase |

TABLE 2

| Gene | Primer Sequence | SEQ ID NO: | Restriction Enzyme |
|---|---|---|---|
| accA | F 5'-TCTAGACGACGGAAGCCTATGAACCCG-3' | 8 | XbaI |
|  | R 5'-GGATCCTTACGGCGCGCCGTAGCTCAT-3' | 9 | BamHI |
| fabD | F 5'-GGTACCCAAGGGACCTATTCAATGTCTGC-3' | 10 | KpnI |
|  | R 5'-GAGCTCTTCTCTCCTTTCTCTCTCTCAGG-3' | 11 | SacI |

TABLE 2-continued

| Gene | Primer Sequence | SEQ ID NO: | Restriction Enzyme |
|---|---|---|---|
| 3.1.2.14 | F 5'-GAGCTCGGAGAGTATTATGGGATTAAGTTA-3' | 12 | SacI |
| | R 5'-GAATTCCTAGTCTATCTCGCTTTCTGTTT-3' | 13 | EcoRI |

The genes of Table 1 were amplified using the primers of Table 2 which were designed to specifically target the genes of interest. Each of these genes contained an RBS (ribosomal binding site) and amplification was completed at 972 bp for accA, at 963 bp for fabD, and at 763 bp for the gene coding for acyl (acyl carrier protein) thioesterase. After starting with one cycle of 95° C./5 min (denaturation), 66° C./1 min (annealing), and 72° C./1 min (extension) under a typical condition (10 mM Tris-HCl (pH 9.0), 50 mM KCl, 0.1% Triton X-100, 2 mM MgSO$_4$, Taq DNA polymerase (DaKaRa)), each PCR was performed with 30 cycles of 95° C./1 min (denaturation), 66° C./30 sec (annealing), and 72° C./1 min (extension). For stable extension, a final cycle of 95° C./1 min (denaturation), 66° C./1 min (annealing), and 72° C./5 min (extension) was carried out. The PCR products thus obtained were identified on 0.8% agarose gel and purified before use in T-vector cloning. The genes of interest were ligated to pGEM-T easy vector (DaKaRa) to construct recombinant plasmids pGEM-T:accA, pGEM-T:fabD, and pGEM-T::3.1.2.14. The recombinant plasmids were transformed into E. coli (AG1 competent cell, Stratagene) to prepare novel strains.

Example 2

Figure 5:
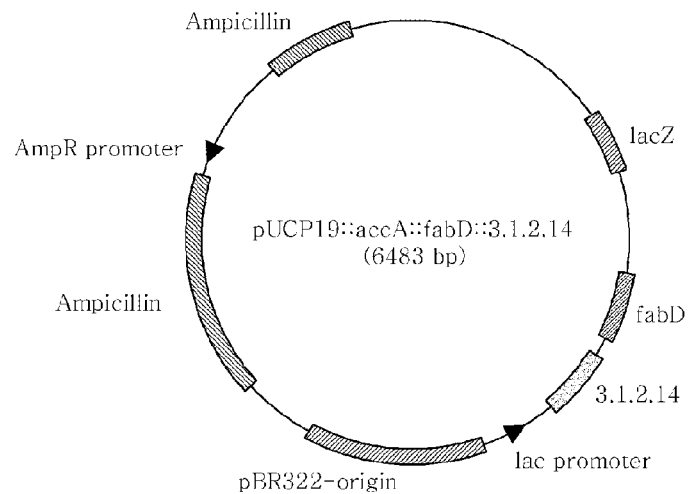
FIG. 5 is a schematic view of the genetic map of the *Escherichia coli-Pseudomonas* shuttle vector pUCP19 transformed with fabD and acyl-acyl carrier protein thioesterase (E.C.3.1.2.14) genes (it is named pJS06 in the present invention.
Figure 6:
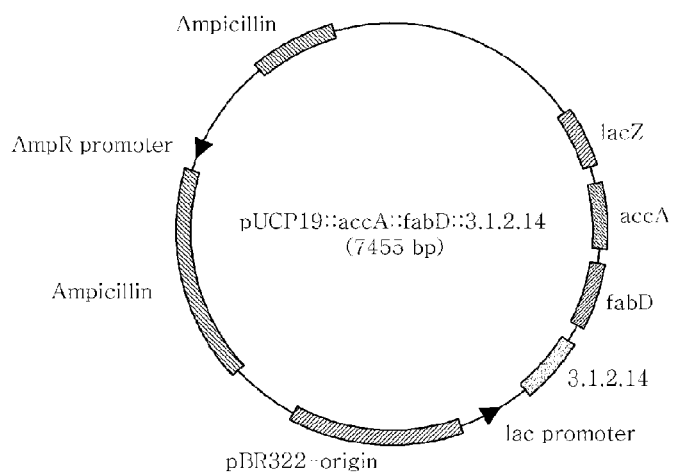
FIG. 6 is a schematic view of the genetic map of the *Escherichia coli-Pseudomonas* shuttle vector pUCP19 transformed with accA, fabD and acyl-acyl carrier protein thioesterase (E.C.3.1.2.14) genes (it is named pJS07 in the present invention).

Construction of Recombinant Plasmids pJS04 and pJS07 pGEM-T::3.1.2.14, pGEM-T:accA, and pGEM-T:fabD, recombinant plasmids of Example 1, and pUCP19 (ATCC, FIG. 2), a shuttle vector for both E. coli and Pseudomonas, were separately treated for 2 hrs with the restriction enzymes of Table 2 in a 37° C. water bath. The resulting DNA digests were inserted into the multi-cloning site of pUCP19, as shown in FIGS. 3 to 5, by ligation at 16° C. using T4 ligase (Dakara). The cloning of each of the genes was examined upon every insertion. After transformation into E. coli (AG1 competent cell, Stratagene), the recombinant plasmid was isolated and digested with the same restriction enzymes as were used for insertion, and the size of the DNA digest was determined on 0.8% agarose gel by electrophoresis.

After digestion with the restriction enzymes of Table 2, the PCR products were introduced into pUCP19 to afford recombinant plasmids pJS04 (carrying the 3.1.2.14 gene) (FIG. 3), pJS05 4 (carrying accA and 3.1.2.14 genes) (FIG. 4), pJS06 (carrying fabD and 3.1.2.14 genes), and pJS07 (carrying accA, fabD and 3.1.2.14 genes) (FIG. 5).

Example 3

Preparation of Pseudomonas aeruginosa Transformant

In consideration of the stability and efficiency of transformation, electroporation was used.

Before electroporation, wild-type Pseudomonas aeruginosa PA14PA14 (ATCC, GenBank NC_008463, Julia M. Plotnikova, et al., Plant Physiol, December 2000, Vol. 124, pp. 1766-1774; Nicole T. Liberati et al., PNAS 103(8):2833-2838 (2006)) was pre-cultured for 16 hrs and 30 µl (0.1%) of the culture was inoculated into 3 mL of LB (10 g/L tryptone, 10 g/L NaCl, 5 g/L yeast extract) and centrifuged to separate cells (12,000 rpm, 1 min) and the medium when absorbance at 600 nm reached 0.6. Then, the cells were washed once with 1 mL of 10% glycerol and harvested by centrifugation (12,000 rpm, 1 min). The cell pellet was resuspended in 80 µL of 10% glycerol. To the suspension was added 1 µL of the recombinant plasmids (pJS04, pJS05, pJS06, and pJS07). The mixtures, each totaling about 80 µl, were placed in respective cuvettes for electroporation (BIO-RAD, Gene pulser cuvette) and electrically shocked using BIO-RAD, Gene pulser Xcell (2500 v, 25 µF, 200Ω). Immediately after applying the electric shock, each of the mixtures was mixed with 1 mL of LB (10 g/L tryptone, 10 g/L NaCl, 5 g/L yeast extract) and incubated at 37° C. 1 hour with agitation at 200 rpm. The cells were cultured at 37° C. on cetrimide agar base (Difco) containing carbenicillin (200 µg/mL) to form single colonies.

Figure 7:
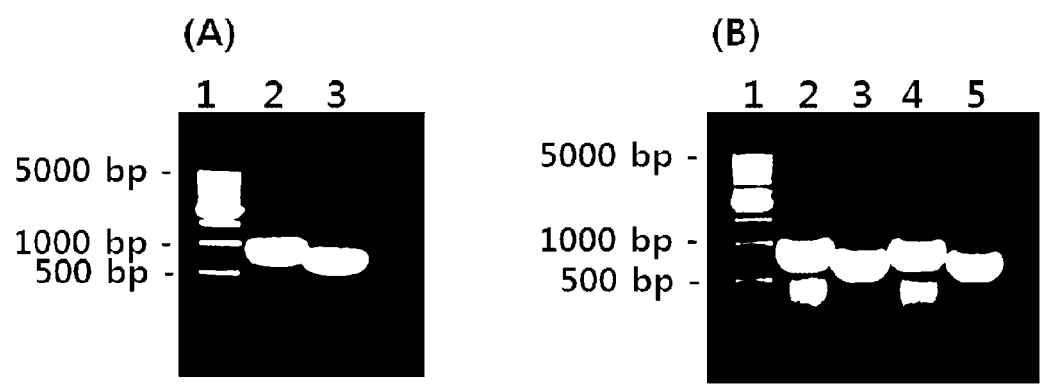
FIG. 7 shows the stable transformation of the recombinant vectors of FIGS. 4 and 5 into *Pseudomonas aeruginosa*, as assayed by PCR.

Thus, the recombinant strains P. aeruginosa SGJS07, P. aeruginosa SGJS08, P. aeruginosa SGJS09 and P. aeruginosa SGJS10 resulting from the transformation of Pseudomonas aeruginosa PA14 with the recombinant plasmids pJS04, pJS05, pJS06 and pJS07, respectively, were obtained (Table 3). To examine whether the genes inserted into the recombinant plasmids were stably expressed in Pseudomonas aeruginosa PA14, the plasmids were isolated from the recombinant strains and were digested with restriction enzymes (FIG. 7).

TABLE 3

Recombinant Strains

| Developed Strain | |
|---|---|
| Pseudomonas aeruginosa SGJS07 | Pseudomonas aeruginosa PA14::pUCP19::3.1.2.14 |
| Pseudomonas aeruginosa SGJS08 | Pseudomonas aeruginosa PA14::pUCP19::accA::3.1.2.14 |
| Pseudomonas aeruginosa SGJS09 | Pseudomonas aeruginosa PA14::pUCP19::fabD::3.1.2.14 |
| Pseudomonas aeruginosa SGJS10 | Pseudomonas aeruginosa PA14::pUCP19::accA::fabD::3.1.2.14 |

Example 4

Culturing of *Pseudomonas aeruginosa* Strain and Protein Production Therefrom Recombinant strains of *Pseudomonas aeruginosa* PA14 (GenBank NC_008463) were pre-cultured for 16 hrs in an LB broth (containing 200 μg/mL carbenicillin). Then, the culture was inoculated into an LB broth (containing 200 μg/mL carbenicillin) and cultured until absorbance at 600 nm reached 0.6-1.0. At this time, the bacterial culture was mixed with a final concentration of 25% glycerol to afford stocks which were stored at −80° C. until use in subsequent experiments.

After being thawed, 30 μL from the stock was cultured in 3 mL of LB containing carbenicillin (200 μg/mL) in a 10 mL bottom tube. Of the culture, 1 mL was inoculated into 200 mL of LB (10 g/L tryptone, 10 g/L NaCl, 5 g/L yeast extract) containing carbenicillin (200 μg/mL) in a 500 mL flask and cultured for 24 hrs at 37° C. with agitation at 170 rpm. For comparison, wild-type *Pseudomonas aeruginosa* PA14 was cultured under the same conditions as in the recombinant strains with the exception that the LB broth was free of carbenicillin. When absorbance at 600 nm of the cultures reached 0.6, protein expression was induced by IPTG (iso-propylthio-β-D-galactoside, sigma, USA) (final concentration of 1 mM/mL). Growth curves of the recombinant *Pseudomonas aeruginosa* strains designed to increase the production of fatty acids by overexpressing enzymes involved in the fatty acid biosynthesis pathway, and the wild-type, are shown in FIG. 8.

As revealed by the curves of FIG. 8, there were no significant differences in growth between the recombinant strains *Pseudomonas aeruginosa* SGJS07, *Pseudomonas aeruginosa* SGJS08, *Pseudomonas aeruginosa* SGJS09 and *Pseudomonas aeruginosa* SGJS10, and the wild-type, indicating that the introduction or overexpression of exogenous genes exerted neither toxicity nor inhibition.

This is thought to be attributable to the fact that the coding region of each gene was designed to have the minimal length required of a nucleotide sequence comprising only indispensible elements, such as RBS and an overexpression function, so that the metabolic burden placed on the host cell was reduced. In addition, the two genes were arranged in the order of their reactions in the biosynthesis pathway.

Example 5

Intracellular Lipid Levels of Wild-Type *Pseudomonas aeruginosa* and Recombinant Strains Lipids were extracted using a modified version of the Bligh-Dyer method (1959). After incubation for 24 hrs in the presence of IPTG under the same conditions as in Example 4, 50 mL of each of the cultures in a 50 mL tube was centrifuged (4500 rpm for 10 min). The cell pellet was suspended in PBS (phosphate-buffer saline, 50 mM, pH 7.4) and centrifuged. The cells of the recombinant strains and the wild-type were vortexed in 2 mL of methanol (MeOH) and then vortexed again together with 1 mL of chloroform ($CHCl_3$). Then, 0.8 mL of sterile distilled water was added to the solution and sufficiently vortexed. Again, this resulting mixture was vigorously mixed with 1 mL of chloroform by vortexing. After centrifugation (4000 rpm for 20 min), the upper layer was withdrawn, transferred into a new tube and dried before carrying out a quantitative analysis of the intracellular lipid levels. This experimental procedure is illustrated in FIG. 9.

All of the recombinant *Pseudomonas aeruginosa* strains of the present invention were observed to have increased lipid content, compared to the wild-type, as can be seen in FIG. 10. Because lipids contain fatty acids, an increased fatty acid content was thought to lead to an increase in lipid content.

The highest lipid content was detected in *Pseudomonas aeruginosa* SGJS14 with the 3.1.2.14 gene of *Streptococcus pyogenes*. Thus, the 3.1.2.14 gene was identified as playing a very important role in the biosynthesis of fatty acids. As described above, the genes involved in the early stage of the fatty acid biosynthesis pathway are cloned, together with the 3.1.2.14 gene in the recombinant strains *Pseudomonas aeruginosa* SGJS08, *Pseudomonas aeruginosa* SGJS09, and *Pseudomonas aeruginosa* SGJS10. The lipid content was found to increase to a relatively higher extent in *Pseudomonas aeruginosa* SGJS08 and *Pseudomonas aeruginosa* SGJS10, both transformed with the accA gene of *Pseudomonas aeruginosa* and to a relatively lesser extent in *Pseudomonas aeruginosa* SGJS09 with the fabD gene of *Pseudomonas aeruginosa*, indicating that the fabD gene of *Pseudomonas aeruginosa* is slightly inhibited in the production of fatty acids, compared to the accA gene.

*Pseudomonas aeruginosa* SGJS08, *Pseudomonas aeruginosa* SGJS09, and *Pseudomonas aeruginosa* SGJS10 in which the genes of *Pseudomonas aeruginosa* and *Streptococcus pyogenes* were co-expressed produced a slightly smaller amount of lipids than did the strain with only the gene of *Streptococcus pyogenes*, which is thought to result from the co-expression of heterogeneous genes.

Example 6

Intracellular Fatty Acid Levels of the Recombinant *Pseudomonas aeruginosa* Strains When sufficient amounts of the cells were obtained 6 and 24 hrs after the incubation in the presence of IPTG under the same conditions as those of Example 4, the extraction of fatty acids from the cells was carried out in the following five steps.

The first step was cell harvesting. Of the culture, 5 mL was centrifuged (4500 rpm, 10 minutes) and the cells thus harvested were stored at −80° C. The next step was saponification. The cells were vortexed for 5-10 sec in 1 mL of Solution 1 (NaOH 45 g, MeOH 150 mL, deionized distilled water 150 mL). After reaction at 100° C. for 5 min, the cells were again vortexed for 5-10 sec. The reaction mixture was maintained at 100° C. for 25 min and then cooled. Thereafter, methylation was carried out. The reaction mixture was mixed vigorously with 2 mL of Solution 2 (6 N HCl 325 mL, MeOH 275 mL) by vortexing for 5-10 sec, followed by reacting at 80° C. for 10 min. Immediately after the reaction, the temperature was reduced. Extraction was the fourth step. The resulting mixture was mixed with 1.25 mL of Solution 3 (Hexane/Methyl tert-Butyl Ester=1/1), followed by shaking up and down for 10 min. The lower layer that was formed thereby was discarded. Finally, washing was performed to facilitate GC analysis. The remaining layer was mixed with 3 mL of Solution 4 (NaOH 10.8 g, ddW 900 mL) and shaken up and down for 5 min. The upper layer thus formed was withdrawn and subjected to GC/MS analysis. For CG/MS analysis, Agilent 7890A gas chromatography with a 5975 series mass-selective detector (MSD) was equipped with HP-5 column (30 m×0.32 mm, film thickness 0.25). GC conditions followed the temperature program of: 40° C. 5 min, to 220° C. at a rate of 3° C./min, to 250° C. at a rate of 3° C. per min, and 250° C. 5 min, and the internal temperature of MS was 160° C. Analysis of the fatty acids extracted from recombinant *Pseudomonas aeruginosa* strains and the wild-type type is shown in FIGS. 11 to 15.

In FIG. 11, various kinds of the fatty acids that were extracted were identified, including hexadecanoic acid (1) and octadecanoic acid (2). In addition, also identified was 9-octadecenoic acid (3). In *Pseudomonas aeruginosa*, octadecanoic acid (2), that is, a fatty acid with 18 carbon atoms, was found to be produced dominantly over 9-octadecenoic acid (3), as shown in FIG. 11.

The predominant fatty acids hexadecanoic acid (C16) (1) and octadecanoic acid (C18) (2) were further quantitatively analyzed against the standard, and the results are given in FIGS. 12 to 14. Hexadecanoic acid contains 16 carbon atoms while octadecanoic acid is a C-18 fatty acid. Also, FIG. 15 shows levels of the fatty acids extracted 6 and 24 hrs after IPTG induction.

As can be seen in FIG. 15, the recombinant *Pseudomonas aeruginosa* strains produced higher levels of both hexadecanoic acid and octadecanoic acid than did the wild-type. Thus, the insertion of a gene coding for the acyl-acyl carrier protein thioesterase of *Streptococcus pyogenes* increased the lipid content.

While levels of the fatty acids produced by *Pseudomonas aeruginosa* SGJS07, *Pseudomonas aeruginosa* SGJS08 and *Pseudomonas aeruginosa* SGJS09, in all of which the *Pseudomonas aeruginosa* gene or genes involved in the early stage of the fatty acid biosynthesis pathway were cloned, were higher than those in the wild-type, but the difference was negligible. When the cells were cultured for a long period of time, e.g., 24 hrs, the amounts of hexanodecanoic acid and octadecanoic acid peaked in *Pseudomonas aeruginosa* SGJS10. While the content of both hexanodecanoic acid and octanodecanoic acid increased in *Pseudomonas aeruginosa* SGJS10 with time, the hexanodecanoic acid content of the wild-type and the other recombinant stains were increased but the octanodecanoic acid content decreased with time.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

INDUSTRIAL APPLICABILITY

As described hitherto, the present invention allows enzymes involved in the fatty acid biosynthesis from glucose to be overexpressed and modifies the metabolic flow by introducing exogenous genes, thus producing a fatty acid in high yield. Thus, the present invention is anticipated to be used for the mass production of fatty acids, useful as a bioenergy source, in an environmentally friendly and economically beneficial manner.

The invention claimed is:

1. A *Pseudomonas aeruginosa* strain, capable of producing a fatty acid in high yield, being transformed with an expression vector carrying a nucleotide sequence coding for acyl-acyl carrier protein thioesterase of *Streptococcus pyogenes*.

2. A *Pseudomonas aeruginosa* strain, capable of producing a fatty acid in high yield, being transformed with an expression vector carrying a nucleotide coding for acetyl-CoA carboxylase carboxytransferase subunit alpha of *Pseudomonas aeruginosa* and a nucleotide sequence coding for acyl-acyl carrier protein thioesterase of *Streptococcus pyogenes*.

3. A *Pseudomonas aeruginosa* strain, capable of producing a fatty acid in high yield, being transformed with an expression vector carrying a nucleotide sequence coding for malonyl-CoA-[acyl-carrier-protein] transacylase of *Pseudomonas aeruginosa* and a nucleotide sequence coding for acyl-acyl carrier protein thioesterase of *Streptococcus pyogenes*.

4. A *Pseudomonas aeruginosa* strain, capable of producing a fatty acid in high yield, being transformed with an expression vector carrying a nucleotide sequence coding for acetyl-CoA carboxylase carboxytransferase subunit alpha of *Pseudomonas aeruginosa*, a nucleotide sequence coding for malonyl-CoA-[acyl-carrier-protein] transacylase of *Pseudomonas aeruginosa*, and a nucleotide sequence coding for acyl-acyl carrier protein thioesterase of *Streptococcus pyogenes*.

5. The *Pseudomonas aeruginosa* strain of claim 1, wherein the expression vector is an *E. coli*-Pseudomonas shuttle vector having a genetic map of FIG. 2, identified as pUCP19.

6. The *Pseudomonas aeruginosa* strain of claim 1, wherein the nucleotide sequence coding for acyl-acyl carrier protein thioesterase is represented by SEQ ID NO: 6.

7. The *Pseudomonas aeruginosa* strain of claim 4, wherein the nucleotide sequence coding for acetyl-CoA carboxylase carboxytransferase subunit alpha is represented by SEQ ID NO: 2.

8. The *Pseudomonas aeruginosa* strain of claim 3, wherein the nucleotide sequence coding for malonyl-CoA-[acyl-carrier-protein] transacylase is represented by SEQ ID NO: 4.

9. The *Pseudomonas aeruginosa* strain of claim 1, being derived from *Pseudomonas aeruginosa* PA14.

10. A method for preparing *Pseudomonas aeruginosa* capable of producing a fatty acid in high yield, comprising:
   i) inserting a nucleotide sequence coding for acyl-acyl carrier protein thioesterase of *Streptococcus pyogenes* into an expression vector; and
   ii) transforming the expression vector of step i) into *Pseudomonas aeruginosa*.

11. A method for preparing *Pseudomonas aeruginosa* capable of producing a fatty acid in high yield, comprising:
   i) inserting into an expression vector either or both of a nucleotide coding for acetyl-CoA carboxylase carboxytransferase subunit alpha and a nucleotide sequence coding for malonyl-CoA-[acyl-carrier-protein] transacylase, and a nucleotide sequence coding for acyl-acyl carrier protein thioesterase of *Streptococcus pyogenes*; and
   ii) transforming the expression vector of step i) into *Pseudomonas aeruginosa*.

12. A method for producing a fatty acid, comprising:
   i) culturing the *Pseudomonas aeruginosa* of claim 1 to allow a fatty acid to be synthesized in the cell; and
   ii) recovering the fatty acid synthesized in step i).

13. The *Pseudomonas aeruginosa* strain of claim 2, wherein the expression vector is an *E. coli*-Pseudomonas shuttle vector having a genetic map of FIG. 2, identified as pUCP19.

14. The *Pseudomonas aeruginosa* strain of claim 3, wherein the expression vector is an *E. coli*-Pseudomonas shuttle vector having a genetic map of FIG. 2, identified as pUCP19.

15. The *Pseudomonas aeruginosa* strain of claim 4, wherein the expression vector is an *E. coli*-Pseudomonas shuttle vector having a genetic map of FIG. 2, identified as pUCP19.

16. The *Pseudomonas aeruginosa* strain of claim 2, wherein the nucleotide sequence coding for acyl-acyl carrier protein thioesterase is represented by SEQ ID NO: 6.

17. The *Pseudomonas aeruginosa* strain of claim 3, wherein the nucleotide sequence coding for acyl-acyl carrier protein thioesterase is represented by SEQ ID NO: 6.

18. The *Pseudomonas aeruginosa* strain of claim 4, wherein the nucleotide sequence coding for acyl-acyl carrier protein thioesterase is represented by SEQ ID NO: 6.

19. The *Pseudomonas aeruginosa* strain of claim 4, wherein the nucleotide sequence coding for acetyl-CoA carboxylase carboxytransferase subunit alpha is represented by SEQ ID NO: 2.

20. The *Pseudomonas aeruginosa* strain of claim 4, wherein the nucleotide sequence coding for malonyl-CoA-[acyl-carrier-protein] transacylase is represented by SEQ ID NO: 4.

21. The *Pseudomonas aeruginosa* strain of claim 2, being derived from *Pseudomonas aeruginosa* PA14.

22. The *Pseudomonas aeruginosa* strain of claim 3, being derived from *Pseudomonas aeruginosa* PA14.

23. The *Pseudomonas aeruginosa* strain of claim 4, being derived from *Pseudomonas aeruginosa* PA14.

24. A method for producing a fatty acid, comprising:
  i) culturing the *Pseudomonas aeruginosa* of claim 2 to allow a fatty acid to be synthesized in the cell; and
  ii) recovering the fatty acid synthesized in step i).

25. A method for producing a fatty acid, comprising:
  i) culturing the *Pseudomonas aeruginosa* of claim 3 to allow a fatty acid to be synthesized in the cell; and
  ii) recovering the fatty acid synthesized in step i).

26. A method for producing a fatty acid, comprising:
  i) culturing the *Pseudomonas aeruginosa* of claim 4 to allow a fatty acid to be synthesized in the cell; and
  ii) recovering the fatty acid synthesized in step i).

\* \* \* \* \*